(12) United States Patent
Smilanich et al.

(10) Patent No.: US 11,835,480 B2
(45) Date of Patent: Dec. 5, 2023

(54) DEVICE FOR DETECTING INSECT LARVAE AND ADULT INSECTS IN STORED PRODUCTS BY SENSING THEIR VOLATILE PHEROMONES AND SEMIOCHEMICALS

(71) Applicant: Sensor Development Corporation, Elyria, OH (US)

(72) Inventors: Nicholas Joseph Smilanich, Rocky River, OH (US); Samuel Firestone Reichert, Brunswick, OH (US); Frank Bernard Tudron, Mentor, OH (US)

(73) Assignee: Sensor Development Corporation, Elyria, OH (US)

( * ) Notice: Subject to any disclaimer, the term of this patent is extended or adjusted under 35 U.S.C. 154(b) by 937 days.

(21) Appl. No.: 16/265,368

(22) Filed: Feb. 1, 2019

(65) Prior Publication Data

US 2019/0234895 A1    Aug. 1, 2019

Related U.S. Application Data

(60) Provisional application No. 62/625,000, filed on Feb. 1, 2018.

(51) Int. Cl.
*G01N 27/12* (2006.01)
*G01N 33/00* (2006.01)
*A01M 99/00* (2006.01)
*A01M 1/02* (2006.01)

(52) U.S. Cl.
CPC ........... *G01N 27/123* (2013.01); *A01M 99/00* (2013.01); *G01N 33/0047* (2013.01); *G01N 33/0073* (2013.01); *A01M 1/026* (2013.01)

(58) Field of Classification Search
CPC ............ G01N 27/123; G01N 33/0047; G01N 33/0073; G01N 33/02; A01M 99/00; A01M 1/026
See application file for complete search history.

(56) References Cited

U.S. PATENT DOCUMENTS

2007/0028667 A1  2/2007  Kim et al.
2015/0323510 A1  11/2015 Huynh et al.
2016/0018356 A1  1/2016  Shankar et al.
2016/0187279 A1  6/2016  Tayebi et al.
(Continued)

FOREIGN PATENT DOCUMENTS

CN   102 706 870        10/2012
EP      2778667 A1       9/2014
(Continued)

OTHER PUBLICATIONS

"Chemical Sensors: An Introduction for Scientists and Engineers," Peter Grundler, Springer (Year: 2007).*
(Continued)

*Primary Examiner* — Benjamin R Schmitt
(74) *Attorney, Agent, or Firm* — Dinsmore & Shohl LLP

(57) ABSTRACT

Minimal-cost, high-accuracy, and portable devices used to detect the presence of insect larvae and adult insects in stored products by sensing gas phase markers such as volatile pheromones, semiochemicals, and kairomones. The methods, devices, and systems disclosed herein utilize a sensor array configured to simultaneously measure a plurality of target markers and filter background gases while remaining compact, highly accurate, and easy to operate.

14 Claims, 24 Drawing Sheets

(56) References Cited

U.S. PATENT DOCUMENTS

| | | | |
|---|---|---|---|
| 2017/0038326 A1* | 2/2017 | Motayed | G01N 33/0047 |
| 2017/0265443 A1 | 9/2017 | Winston, III | |
| 2017/0284999 A1* | 10/2017 | Maric | G01N 33/0047 |
| 2018/0003660 A1* | 1/2018 | Tayebi | G01N 33/0047 |
| 2019/0234895 A1 | 8/2019 | Smilanich | |

FOREIGN PATENT DOCUMENTS

| | | |
|---|---|---|
| JP | 2015-200647 A | 11/2015 |
| JP | 2017-166826 A | 9/2017 |
| TW | 201831890 A | 9/2018 |
| WO | WO 2008/091306 | 7/2008 |

OTHER PUBLICATIONS

Engineering Tool Box, (2010). "Resistance vs. Conductance" [online] Available at: https://www.engineeringtoolbox.com/resistance-conductance-d_1654.html (Year: 2010).*

International Search Report for corresponding PCT application No. PCT/US2020/047911 dated Dec. 9, 2020.

Smilanich; "Stored Product Protection with a Pheromone Based Multi-Insect Detector"; Jan. 31, 2017; pp. 1-4.

Wu et al.; "Feasibility of the application of electronic nose technology to detect insect infestation in wheat"; Dec. 31, 2013; pp. 3.1-3.9; Canadian Biosystems Engineering, vol. 55, No. 1.

Zhou et al.; "Detection of Insect Infestations in Paddy Field using an Electronic Nose"; Oct. 31, 2011; pp. 1560-8530; International Journal of Agriculture and Biology.

TW Office Action, dated Oct. 4, 2023 pertaining to Taiwan Patent Application No. 109103037.

\* cited by examiner

DEVICE FOR DETECTING INSECT LARVAE AND ADULT INSECTS IN STORED PRODUCTS BY SENSING THEIR VOLATILE PHEROMONES AND SEMIOCHEMICALS

CROSS-REFERENCE TO RELATED APPLICATIONS

This application claims priority to U.S. Provisional Patent Application Ser. No. 62/625,000, filed on Feb. 1, 2018, entitled A DEVICE FOR DETECTING INSECT LARVAE AND ADULT INSECTS IN STORED PRODUCTS BY SENSING THEIR VOLATILE PHEROMONES AND SEMIOCHEMICALS, the entire disclosure of which is incorporated by reference herein.

BACKGROUND

The following disclosure relates generally to the insect and insect infestation detection arts, chemical sensing arts, gas detection arts, volatile organic compound analysis arts, gas-sensing microchip arrays, and methods and devices related thereto. It finds particular application in association with arts related to the high sensitivity and selectivity detection of insects in stored food and other products or materials.

Stored product insects ("SPIs") are most often found feeding on finished food products, the ingredients for food or are infesting equipment where food is prepared, processed, packaged or stored. The economic losses from these pests in the processing, transportation, and storage systems can be in the millions of dollars per incident of contamination, product recall, consumer complaint/litigation, and pest control applications (Arthur et. al., 2009). Additionally, certain SPIs have health implications if accidently consumed, causing gastric stress in infants and elderly people (Okamura, 1967).

Current insect detection relies on flashlight inspection and the use of traps with multiple synthetic pheromone lures and traps to capture adult SPI. The pheromones are volatile organic compounds ("VOCs") that are emitted from male and or females of the individual species. Pheromone lures and traps rely on insect activity and this can be significantly affected by temperature. Pheromone volatility, quantity/quality, as well as human activity and insect dynamics interplay with these elements resulting in trap data that is quite variable. Interpretation of trap catch is based on a small sampling of the population (2-10% or less). This makes detection and remediation of pest infestations difficult.

The Indianmeal moth ("IMM") is the most common stored product insect found throughout the U.S. (Mueller, 1998; Resener 1996). It is the one insect found more often than any other on stored food and grain in the U.S. The adult IMM can be found almost anywhere in the temperate regions of the world. Further, in the U.S. and Europe it is the one insect pest that causes the most damage. There are two reasons that this insect has survived so well in our environment: 1) the large number of eggs the female lays in her short life time; and 2) its ability to genetically change or adapt to survive pesticides which man uses to protect his food (resistance). The IMM was found to be the most resistant insect known to man. Over a fifty-year period, the genetic makeup of this insect has been changed to resist the commonly used pesticide Malathion. In the 1970's, the IMM started showing signs of resistance to this commonly used insecticide. The IMM developed a 60,000-fold resistance to this pesticide.

The IMM are most often found feeding on finished food products, the ingredients for food such as stored wheat products, milled/processed wheat, and other stored products such as milled cereal products, flour, bran, pasta products, spices, or infesting equipment where food is prepared, processed, packaged or stored. IMM larvae are the destructive life stage of the insect, eating voraciously. The larvae are highly mobile and can continuously seek out new sources of food. The value of the food is damaged by the food they consume, the frass they deposit, and the webbing that the larvae leave behind as they move Further, the IMM is often a precursor of other stored product insects. An un-treated IMM infestation can be an indicator of other SPI infestations yet to come (Mueller, 2016). The five most commonly encountered stored product insects (SPI) include the Indianmeal moth (*Plodia interpunctella*), warehouse beetle (*Trogoderma variabile*), flour beetles (*Tribolium* spp.), grain beetles (*Oryzaephilus* spp.) and the cigarette beetle (*Lasioderma serricorne*) (Mueller, 1998; Hagstrum and Subramanyam, 2006). The economic losses from these pests in processing, transporting and storing can be in the millions of dollars per incident of contamination, product recall, consumer complaint/litigation, and pest control applications (Arthur, 2009). Yet there is no efficient, low cost method to monitor and detect them.

Several SPI pheromones have been identified but are not commercially available due to short shelf life and cost of production (Phillips et. al., 2000). The compounds are unique but can attract interspecific competitors such as in the stored food moth group and the *Trogoderma* complex. The single pheromone (Z,E)-9,12-Tetradecadienyl acetate is the predominant pheromone for *Plodia*, but will attract three other food moths of the *Ephestia* species. The pheromone compound R,Z 14-Methyl-8-Hexadecenal is the main component for attracting the warehouse beetle (*Trogoderma variabile*), but will also attract three other common *Trogoderma* species including a quarantine pest (Khapra beetle, *Trogoderma granarium*). Several species of flour beetles (*Tribolium* species) are attracted to a single compound 4,8-Dimethyldecanal, two species of grain beetles (*Oryzaephilus* species) are attracted to (Z,Z)-3,6-Dodecadien-11-olide, but (4S,6S,7S)-4,6-Dimethyl-7-hydroxynona-3-one, the pheromone for cigarette beetles (*Lasioderma serricorne*) is unique to the species.

Furthermore, with respect to possible target semiochemicals and/or kairomones, these semiochemicals and kairomones are high molecular weight VOCs. Thus, their vapor pressures and concentrations in the headspace over infested stored products will be low, and thus are much more difficult to detect.

Thus, it would be desirable to eliminate the variability and uncertainty of detecting pest presence/absence, abundance, and location by using methods, devices, and systems that can detect and measure multiple pheromone concentrations. Additionally, it would be desirable provide such methods, devices, and systems that can detect other stored product insect larvae by sensing their semiochemicals/kairomones in an analogous fashion. Threshold concentrations can be established to determine immediate absence or presence of the most common SPI within a trailer, land/sea container, bulk tote, pallet of bagged ingredients or a storage room. It would also be desirable to provide the ability to detect a gradient of VOC concentrations, which could assist in locating and pinpointing SPI infestations within structures, wall voids, crack and crevices or equipment. Further, it is desirable to provide a handheld device, which would remove much of the dependency of insect mobility and environmental as factors that affect activity from the SPI monitoring model.

INCORPORATION BY REFERENCE

The following references, the disclosures of which are incorporated in their entireties by reference, are mentioned:
Arthur F. H. Johnson J. A. Neven L. G. Hallman G. J. Follett P. A. (2009). Insect Pest Management in Postharvest Ecosystems in the United States of America. *Outlooks on Pest Management,* 20: 279-284.
Hagstrum D. W. and Subramanyam B. (2006). *Fundamentals of Stored-Product Entomology.* St. Paul: AACC Int.
Mueller, David K (1998). *Stored Product Protection: A Period of Transition.* Insects Limited, Indianapolis, Ind.
Okumura, G. T. (1967). A Report of Canthariasis and Allergy Caused by *Trogoderma* (Coleoptera: Dermestidae). *California Vector Views,* Vol. 14 No. 3, pp. 19-22.
Phillips, T. W., Cogan, P. M. and Fadamiro, H. Y. (2000). Pheromones in B. Subramanyam and D. W. Hagstrum (Eds.). *Alternatives to Pesticides in Stored-Product IPM,* pp. 273-302 Kluwer Academic Publishers, Boston, MA
Resener, A. M. (1997). National Survey of Stored Product Insects. Fumigants and Pheromones, Issue 46, pp 3-4.

BRIEF DESCRIPTION

Disclosed in various embodiments herein are low-cost and high-accuracy methods, devices, and systems for identifying insect infestations of a stored product (e.g. food) based on the detection of one or more target volatile organic compounds ("VOCs") within a target fluid flow (e.g. air sample) sampled from a region proximate to the stored product. The disclosed methods, systems, and devices having minimal cost and high accuracy enables widespread application of real-time, non-invasive, detection of insect larva semiochemicals/kairomones or adult insect pheromones in settings where products are stored.

In accordance with a first embodiment of the present disclosure, there is provided a method of identifying an insect infestation of a stored product by detecting one or more target VOCs within a target fluid flow, the method comprising the steps of: providing a device that comprises a sensor array having a plurality of VOC sensors; heating one or more of the plurality of VOC sensors to at least a first operating temperature; contacting the one or more VOC sensors with the target fluid flow; determining a set of conductance change values corresponding to each of the one or more VOC sensors contacted with the target fluid flow; and determining a gas component concentration for one or more of the target VOCs within the target fluid flow based on the set of conductance change values. Further, each of the VOC sensors of the sensor array provided includes: a substrate having a first and second side; a resistive heater circuit formed on the first side of the substrate; a sensing circuit formed on the second side of the substrate; and a chemically sensitive film formed over the sensing circuit on the second side of the substrate. In particular embodiments, the method can include correcting the baseline resistance of the VOC sensors to an earlier baseline value after sampling VOC markers in a fluid flow, which may be accomplished by adjusting the operating temperature of one or more VOC sensors after each sampling of the target VOCs.

In accordance with another embodiment of the present disclosure, there is provided a device for detecting one or more target VOCs within a target fluid flow, the device comprising a sensor array having a plurality of VOC sensors, wherein each VOC sensor includes: a substrate; a resistive heater circuit formed on a first side of the substrate; a sensing circuit formed on a second side of the substrate; and a chemically sensitive film formed over the sensing circuit on the second side of the substrate.

In accordance with still another embodiment of the present disclosure, there is provided a system for identifying an insect infestation of a stored product, the system comprising: a testing chamber enclosing a sensor array; an air transfer unit configured to retrieve a fluid flow and deliver the fluid flow to the testing chamber; and a controller operatively connected to the air transfer unit and the sensor array. The sensor array includes a plurality of VOC sensors, and the controller is configured to: operate the air transfer unit to retrieve the fluid flow from a target area and deliver the fluid flow to the testing chamber; operate the sensor array to measure a conductance for one or more of the plurality of VOC sensors; determine a set of conductance change values corresponding to each of the one or more VOC sensors; and determine a gas component concentration for one or more target VOCs within the fluid flow based on the set of conductance change values.

BRIEF DESCRIPTION OF THE DRAWINGS

The subject disclosure may take form in various components and arrangements of components, and in various steps and arrangement of steps. The drawings are only for purposes of illustrating the preferred embodiments and are not to be construed as limiting the subject disclosure.

DETAILED DESCRIPTION

Figure 1:
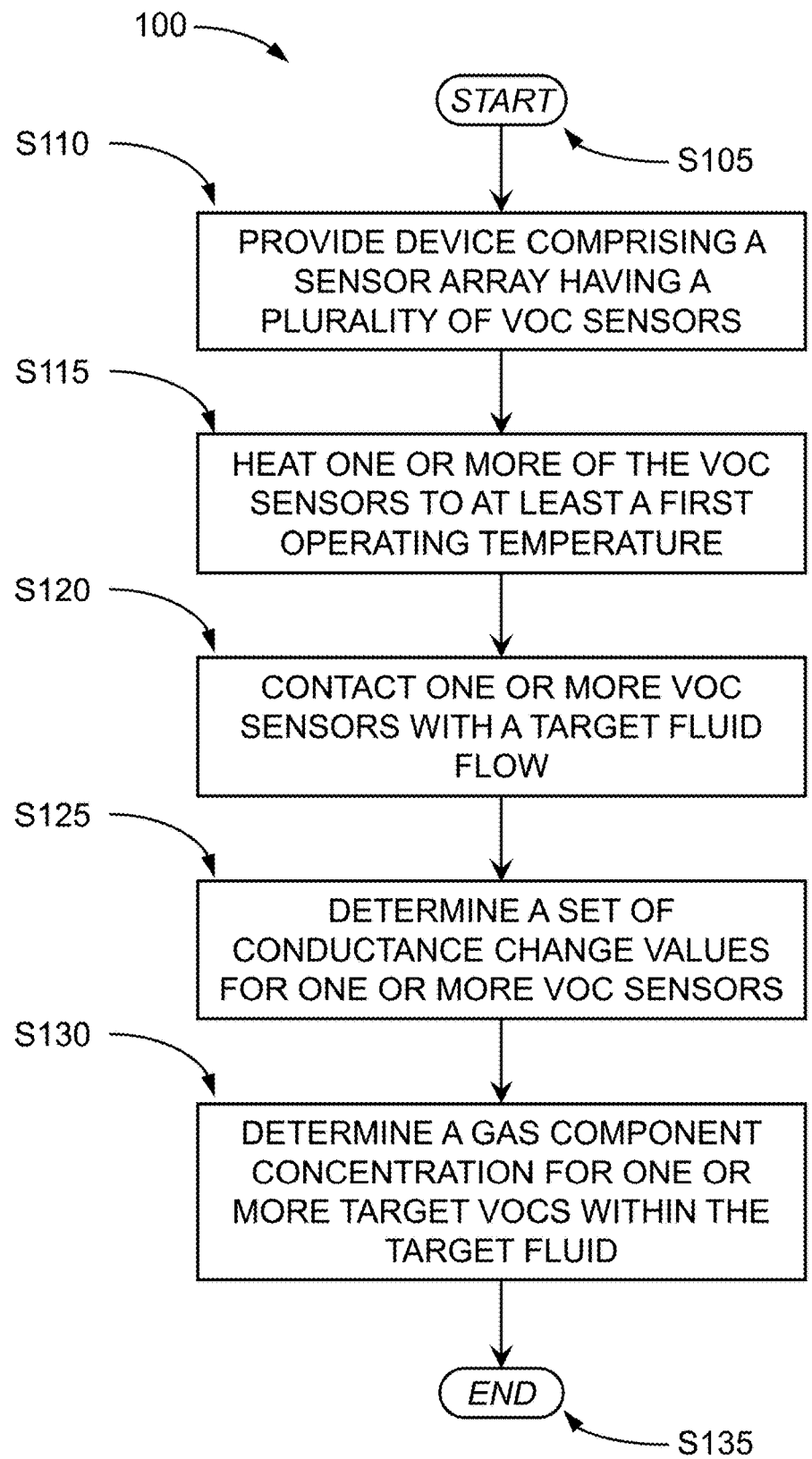
FIG. 1 is a flow chart illustrating a method of identifying an insect infestation in accordance with one embodiment of the subject application.

In the following specification and the claims which follow, reference will be made to a number of terms which shall be defined to have the following meanings.

Definitions

In the following specification and the claims that follow, reference will be made to a number of terms which shall be defined to have the following meanings. Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function. Furthermore, it should be understood that the drawings are not to scale.

The singular forms "a," "an," and "the" include plural referents unless the context clearly dictates otherwise.

The term "comprising" is used herein as requiring the presence of the named components/steps and allowing the presence of other components/steps. The term "comprising" should be construed to include the term "consisting of", which allows the presence of only the named components/steps.

Numerical values should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently combinable (for example, the range of "from 2 mm to 10 mm" is inclusive of the endpoints, 2 mm and 10 mm, and all the intermediate values).

The term "about" can be used to include any numerical value that can vary without changing the basic function of that value. When used with a range, "about" also discloses the range defined by the absolute values of the two endpoints, e.g. "about 2 to about 4" also discloses the range "from 2 to 4." More specifically, the term "about" may refer to plus or minus 10% of the indicated number.

The terms "ppm" and "ppb" should be understood to refer to "parts per million" and "parts per billion" respectively. As used herein, "ppm", "ppb", and the like refer to a volume fraction, rather than a mass fraction or mole fraction. For example, the value 1 ppm may be expressed as 1 µV/V, and the value 1 ppb may be expressed as 1 nV/V.

The present disclosure may be understood more readily by reference to the following detailed description and the various drawings discussed therein.

Methods

Disclosed herein are methods of determining whether an insect infestation is present in a stored product by detecting the presence of one or more target volatile organic compounds ("VOCs"), such as certain semiochemicals, kairomones, and/or pheromones of various stored product insects ("SPIs"), with high sensitivity and high selectively.

With reference to FIG. 1, a method 100 of identifying an insect infestation of a stored product by detecting one or more target volatile organic compounds within a target fluid flow is provided. The method includes: providing a device comprising a sensor array having a plurality of VOC sensors (S110); heating one or more of the plurality of VOC sensors to at least a first operating temperature (S115); contacting the one or more VOC sensors with the target fluid flow (S120); determining a set of conductance change values corresponding to each of the one or more VOC sensors contacted with the target fluid flow (S125); and determining a gas component concentration for one or more of the target VOCs within the target fluid flow based on the set of conductance change values (S130). In accordance with a first embodiment of the method 100, each of the VOC sensors of the sensor array comprises: a substrate; a resistive heater circuit; a sensing circuit; and a chemically sensitive film formed over the sensing circuit. In some embodiments, the resistive heater circuit may be formed on a first side of the substrate, the sensing circuit may be formed on a second side of the substrate, and the chemically sensitive film may be formed over the sensing circuit on the second side of the substrate.

In particular embodiments, the method 100 includes measuring a signal conductance for the one or more VOC sensors after contacting the one or more VOC sensors with the target fluid flow. That is, the set of conductance change values may be determined based on the difference between the signal conductance for each of the one or more VOC sensors contacted with the target fluid flow and a baseline conductance of each of the corresponding VOC sensors. In some embodiments, the baseline conductance for one or more VOC sensors is measured while the one or more VOC sensors are in an atmosphere absent of any target VOCs.

In preferred embodiments, the target fluid flow is an air sample taken from within a proximity to the stored product being evaluated for possible insect infestation. That is, the target fluid flow may be a gas sample from the headspace over the stored product of interest.

The method 100 begins at S105 and ends at S135, however, in particular embodiments, the method 100 may be repeated (e.g. repeating steps S110 to S130) by sampling a plurality of target fluid flows (e.g. air samples) from within a plurality of proximities to the stored product(s) being evaluated. That is, the method 100 may identify a gradient of potential insect infestation by sampling one or more target fluid flows at a plurality of distances from the stored product(s) (e.g. at a distance less than about 1 foot from the stored product; at a distance between about 1 foot and 2 feet from the stored product; at distance between about 2 feet and 3 feet from the stored product; etc.).

In further embodiments, the one or more target VOCs are a semiochemical, a kairomone, and/or a pheromone associated with one or more insects such as SPIs. In particular, the one or more target VOCs may be a semiochemical, a kairomone, and/or a pheromone associated with the red flour beetle, sawtoothed grain beetle, warehouse beetle, Indian-meal moth, and/or cigarette beetle, for example. In specific embodiments, the at least one of the one or more target VOCs within a fluid flow may be selected from a group consisting of: 4,8-dimethyldecanal; (Z,Z)-3,6-(11R)-Dodecadien-11-olide; (Z,Z)-3,6-Dodecadien-olide; (Z,Z)-5,8-(11R)-Tetradecadien-13-olide; (Z)-5-Tetradecen-13-olide; (R)—(Z)-14-Methyl-8-hexadecenal; (R)-(E)-14-Methyl-8-hexadecen-al; γ-ethyl-γ-butyrol-actone; (Z,E)-9,12-Tetradecadienyl acetate; (Z,E)-9,12-Tetra-decadien-1-ol; (Z,E)-9,12-Tetradecadienal; (Z)-9-Tetradecenyl acetate; (Z)-11-Hexa-decenyl acetate; (2S,3R,1'S)-2,3-Dihydro-3,5-dimethyl-2-ethyl-6(1-methyl-2-oxobutyl)-4H-pyran-4-one; (2S,3R,1'R)-2,3-Dihydro-3,5-dimethyl-2-ethyl-6(1-methyl-2-oxobutyl)-4H-pyran-4-one; (4S,6S,7S)-7-Hydroxy-4,6-dimethylnonan-3-one; (2S,3S)-2,6-Diethyl-3,5-dimethyl-3,4-dihydro-2H-pyran; 2-Palmitoyl-cyclohexane-1,3-dione; and 2-Oleoyl-cyclo-hexane-1,3-dione.

Figure 2A:
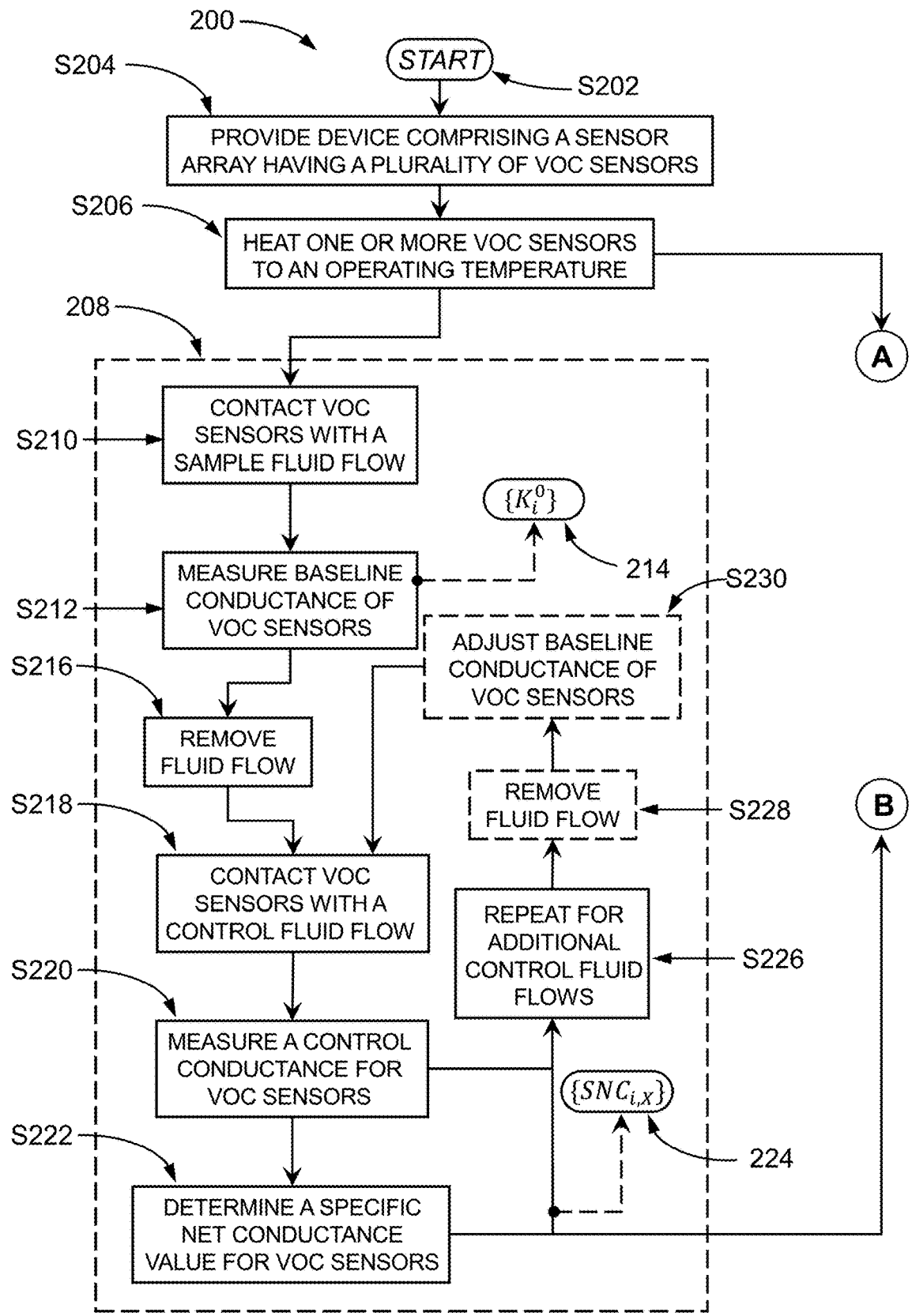
FIGS. 2A-2B are flow charts illustrating a further method of identifying an insect infestation in accordance with a further embodiment of the subject application.
Figure 2B:
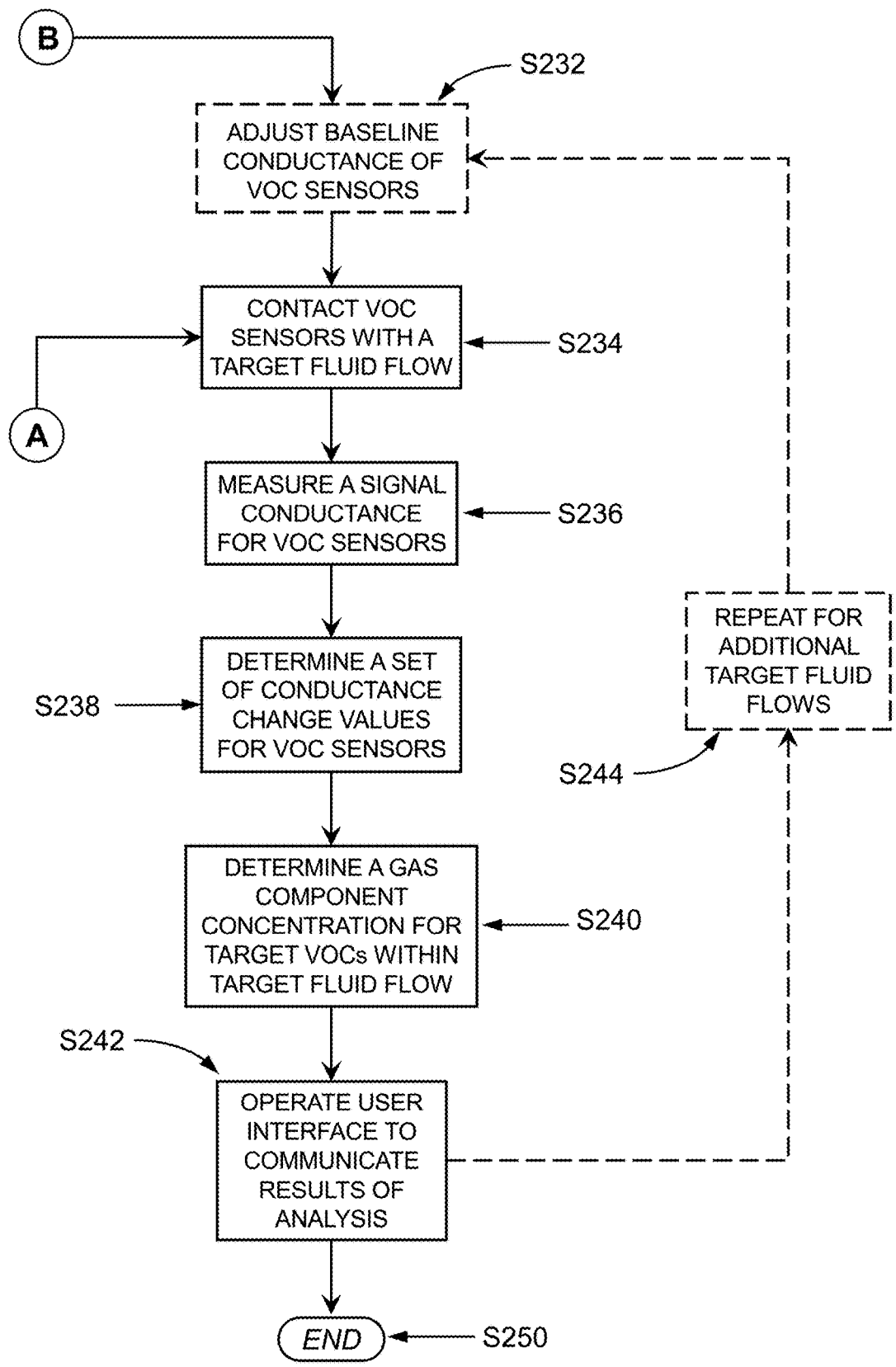

With reference to FIGS. 2A and 2B, a method 200 of identifying an insect infestation of a stored product by detecting one or more target volatile organic compounds within a target fluid flow is provided in accordance with a further embodiment of the present disclosure. The method 200 begins at S202.

In a step S04, a device comprising a sensor array having a plurality of VOC sensors is provided. Each of the VOC sensors of the sensor array comprises: a substrate; a resistive heater circuit; a sensing circuit; and a chemically sensitive film formed over the sensing circuit. In some embodiments, the resistive heater circuit may be formed on a first side of the substrate, the sensing circuit may be formed on a second side of the substrate, and the chemically sensitive film may be formed over the sensing circuit on the second side of the substrate.

In particular embodiments, the sensor array includes a plurality of differentiated VOC sensors. That is, the surface composition for one or more of the plurality of VOC sensors may be varied through the inclusion of catalytic materials in the chemically sensitive film (i.e. active layer). In other words, chemically sensitive film of one or more VOC sensors can comprise a doping agent. In some embodiments, the doping agent may be, for example, a transition metal. For example, the doping agent may be selected from a group consisting of: platinum; palladium; molybdenum; tungsten; nickel; ruthenium; and osmium.

In a step S206, one or more of the plurality of VOC sensors are heated to at least a first operating temperature. In particular embodiments, the operating temperature is between about 180° C. and about 400° C. In further embodiments, the operating temperature of the one or more VOC sensors is maintained during subsequent steps of the method. In particular, the heating circuit of each VOC sensor may be utilized to measure and control the temperature of the VOC sensor throughout its operation.

In particular embodiments of the method 200, the method may include one or more calibration steps 208, comprising: contacting one or more of the plurality of VOC sensors with a sample fluid flow, the sample fluid flow being absent of any target VOCs (S210); measuring a baseline conductance for one or more VOC sensors (S212); optionally removing the fluid flow from contact with the one or more VOC sensors (S216); contacting the one or more VOC sensors with a control fluid flow having a known concentration of the target VOC (S218); measuring a control conductance for each of the one or more VOC sensors (S220); calculating a specific net conductance value based on the measured control conductance of the VOC sensor and the known concentration of the target VOC within the control fluid flow (S222); and repeats at least steps S218 to S222 for a plurality of control fluid flows (S226). The calibration steps 208 may further comprise: removing the fluid flow from contact with the one or more VOC sensors (S228); and adjusting the baseline conductance of one or more VOC sensors (S230) after contact with at least one target VOC.

In a step S210, one or more of the plurality of VOC sensors are contacted with a sample fluid flow. In preferred embodiments, the sample fluid flow is a volume of air without any target VOCs for which the method 200 may be testing.

In a step S212, a baseline conductance for the one or more VOC sensors contacted with the sample fluid flow is measured using the sensing circuits of the VOC sensors. Because the film formed over the sensing circuit of the VOC sensors is chemically sensitive (e.g. semiconductive), the current flowing in the material is due to electrons in the film's conduction band, which may be affected by the presence of undesirable and/or targeted compounds (e.g. target VOCs). Thus, after attaining operating temperature in a step S206, and in contact with a gas sample (i.e. sample fluid flow) that does not contain the marker gas (i.e. fluid flows having at least one target VOC), the VOC sensor's resistance is measured and recorded as a baseline resistance or a baseline conductance. In some embodiments, a set of baseline conductances ($\{K_i^0\}$) 214 is determined and includes a baseline conductance (e.g. $K_1^0, K_2^0, \ldots K_n^0$) for each of the plurality of VOC sensors.

In a step S216, the sample fluid flow is removed from contact with the VOC sensors of the sensor array. In particular embodiments, this may include purging a chamber or reactor housing the sensor array and/or one or more of the VOC sensors.

In a step S218, one or more VOC sensors are contacted with a control fluid flow (e.g. marker gas) having a known concentration of at least one target VOC.

In a step S220, a control conductance for each of the one or more VOC sensors contacted with the control fluid flow is measured. Because contact with the control fluid flow may make greater or fewer electrons available to the conduction based of the chemically sensitive film, the VOC sensor's resistance/conductance changes.

Then, in a step S222, a specific net conductance value for each of the one or more VOC sensors is determined based on the measured test conductance of the VOC sensor and the known concentration of the target VOC within the control fluid flow. As investigated and disclosed herein, the amount of the conductance change may be proportional to the concentration of the gas, with the specific net conductance ("SNC") as used herein refers to the proportionality coefficient. In particular embodiments, the control fluid flow has a first target VOC concentration of about 10 ppb to about 400 ppb. In preferred embodiments, the control fluid flow has a target VOC concentration of about 200 ppb.

The resulting change between the baseline conductance and the control conductance measured for one or more of the plurality of VOC sensors is determined and divided by the specified (i.e. known) concentration to give a SNC value (i.e. a measure of sensitivity of that chip for that gas) with units generally expressed as "nano-mhos/part per billion" or "nmho/ppb". Each chip will have a different SNC for each of the target gases of interest in the application.

For further calibration, in a step S226, at least steps S218 to S222 may be repeated for additional control fluid flows to obtain a plurality of specific net conductance ("SNC") values for one or more of the VOC sensors, wherein each of the specific net conductance values for each of the VOC sensors corresponds to a different target VOC. In some embodiments, the plurality of SNC values is a set of SNC values (($SNC_{i,x}$)) 224 and includes SNC values corresponding to one or more target VOCs for each of the plurality of VOC sensors (e.g. for a first VOC sensor, $SNC_{1,X_1}$, $SNC_{1,X_2}$, ... $SNC_{1,X_n}$; for a second VOC sensor, $SNC_{2,X_1}$, $SNC_{2,X_2}$, ... $SNC_{2,X_n}$; etc.), wherein $X_n$ represents a particular target VOC.

The method 200 may also include a step that comprises adjusting the baseline conductance/resistance of one or more of the VOC sensors (S230/S232). For example, after being contacted with a target VOC(s), a VOC sensor may have a subsequent (i.e. post-contact) baseline conductance different from its baseline conductance prior to contact with the target VOC(s). In particular embodiments, such baseline conductance variations may be accounted for by adjusting the baseline conductance after contact with the target VOC(s) in a step S230/S232. During calibration 208, the control fluid flow may be removed S228 (e.g. from the sensor array chamber), and the conductance of the VOC sensors may be adjusted in a step S230 by measuring the conductance of each of the VOC sensors to determine a post-contact conductance for the VOC sensors, comparing the post-contact conductances with the baseline conductances 214, and heating one or more of the VOC sensors to at least a second operating temperature such that the conductance of each of the VOC sensors at a second operating temperature matches the corresponding baseline conductance 214 prior to contact. The second operating temperature for each of the VOC sensors may be higher or lower than the first operating temperature of the corresponding VOC sensor, based on the measured post-contact conductance of that VOC sensor.

Turning to FIG. 2B, after calibration steps 208 the baseline conductance of the VOC sensors may be adjusted in a step S232 by clearing the sensor array chamber of target VOCs, measuring the conductance of one or more VOC sensors, comparing the measured conductances with the corresponding baseline conductances, and heating one or more of the VOC sensors to at least a second operating temperature such that the conductance of each of the VOC sensors at the second operating temperature matches the corresponding baseline conductance 214.

Following the adjustment step S232 or the heating step S206, one or more VOC sensors are contacted with a target fluid flow at a step S234. In particular embodiments, the target fluid flow is an air sample taken from within a proximity to the stored product being evaluated for possible insect infestation. As such, the target fluid flow may contain one or more target VOCs, such as a semiochemical, a kairomone, and/or a pheromone associated with one or more insects (e.g. SPIs). For example, several pheromones and semiochemicals are listed below in Table 1 and Table 2 for certain SPIs:

TABLE 1

SPIs and their Pheromones

| PEST | PHEROMONE | CHEMICAL NAME |
|---|---|---|
| Red flour beetle *Triboleum castaneum* | tribolure | 4,8-Dimethyldecanal |
| Sawtoothed grain beetle *Oryzaephilus surinamensis* | cucujolide IV | (Z,Z)-3,6-(11R)-Dodecadien-11-olide |
| | cucujolide IX | (Z,Z)-3,6-Dodecadienolide |
| | cucujolide V | (Z,Z)-5,8-(11R)-Tetradecadien-13-olide |
| | cucujolide III | (Z)-5-Tetradecen-13-olide |
| Warehouse beetle *Trogoderma variabile Ballion* | R,Z-trogodermal | (R)-(Z)-14-Methyl-8-hexadecenal |
| | R,E-trogodermal | (R)-(E)-14-Methyl-8-hexadecenal |
| | γ-caprolactone | γ-ethyl-γ-butyrolactone |

TABLE 1-continued

SPIs and their Pheromones

| PEST | PHEROMONE | CHEMICAL NAME |
|---|---|---|
| Indian meal moth *Plodia interpunctella* | Z9E12-14Ac | (Z,E)-9,12-Tetradecadienyl acetate |
| | Z9E12-14OH | (Z,E)-9,12-Tetradecadien-1-ol |
| | Z9E12-14Ald | (Z,E)-9,12-Tetradecadienal |
| | Z9-14Ac | (Z)-9-Tetradecenyl acetate |
| | Z11-16Ac | (Z)-11-Hexadecenyl acetate |

TABLE 1

SPIs and their Pheromones

| PEST | PHEROMONE | CHEMICAL NAME |
|---|---|---|
| Cigarette beetle *Lasioderma serricorne* (F.) | α-serricorone | (2S,3R,1'S)-2,3-Dihydro-3,5-dimethyl-2-ethyl-6(1-methyl-2-oxobutyl)-4H-pyran-4-one |
| | β-serricorone | (2S,3R,1'R)-2,3-Dihydro-3,5-dimethyl-2-ethyl-6(1-methyl-2-oxobutyl)-4H-pyran-4-one |
| | 4S6S7S-serricornin | (4S,6S,7S)-7-Hydroxy-4,6-dimethylnonan-3-one |
| | anhydroserricornin | (2S,3S)-2,6-Diethyl-3,5-dimethyl-3,4-dihydro-2H-pyran |
| | 2S3R-serricorone | (2S,3R)-2,3-Dihydro-3,5-dimethyl-2-ethyl-6-(1-methyl-2-oxobutyl)-4H-pyran-4-one |

TABLE 2

IMM Pheromone and Semiochemical Components

| | Adult Indian meal moth *Plodia interpunctella* | Indian meal moth larvae *Plodia interpunctella* |
|---|---|---|
| PHEROMONE COMPONENT | 9,12-Tetradecadienyl acetate 9,12-Tetradecadien-1-ol 9,12-Tetradecadienal (Z)-9-Tetradecenyl acetate (Z)-11-Hexadecenyl acetate | |
| SEMIOCHEMICAL COMPONENT | | 2-Palmitoyl-cyclohexane-1,3-dione 2-Oleoyl-cyclohexane-1,3-dione |

At a step S236, a signal conductance is measured for the one or more VOC sensors after contacting the one or more VOC sensors with the target fluid flow.

Then, at a step S238, a set of conductance change values ($\{\Delta K_i\}$) is determined for one or more of the VOC sensors of the sensor array. In particular embodiments, for each of the VOC sensors, the conductance change value may be determined as shown below:

$$\Delta K_i = K_i - K_i^0$$

wherein i is an integer, $\Delta K_i$ is the conductance change value for VOC sensor i, $K_i$ is the signal conductance of the VOC sensor i measured in the present of the target fluid flow, and $K_i^0$ is the baseline conductance for the VOC sensor i.

In a step S240, a gas component concentration ($[X]_n$) for one or more of the target VOCs within the target fluid flow is determined based on the set of conductance change values. In particular embodiments, more than one target VOC may be present in the target fluid flow, in additional to other background and/or interferent gases, making analysis difficult. In particular embodiments, the gas component concentrations ($[X]_n$) for the one or more target VOCs within the target fluid flow is determined based on the set of conductance change values and the one or more SNCs for each of the VOC sensors. In further embodiments, the gas component concentrations ($[X]_n$) for the one or more target VOCs within the target fluid flow is determined by solving a system of equations, for example, as illustrated below:

$$\Delta K_1 = SNC_{1A}[A] + SNC_{1B}[B] + SNC_{1C}[C] + SNC_{1D}[D]$$

$$\Delta K_2 = SNC_{2A}[A] + SNC_{2B}[B] + SNC_{2C}[C] + SNC_{2D}[D]$$

$$\Delta K_3 = SNC_{3A}[A] + SNC_{3B}[B] + SNC_{3C}[C] + SNC_{3D}[D]$$

$$\Delta K_4 = SNC_{3A}[A] + SNC_{4B}[B] + SNC_{4C}[C] + SNC_{4D}[D]$$

wherein $\Delta K_i$ is the measured conductance change for sensor "i", "i" ranging from 1 to 4, $SNC_{ij}$ is the "Specific Net Conductance" of sensor "i" when contacted by gas (e.g. target VOC) "j", "j" being gas or gas category A, B, C or D, and [X] is the concentration of gas A, B, C, or D expressed in gas volume-to-volume terms, that is, liters of gas per liter of total atmosphere.

Although only four target VOCs (i.e. A, B, C, and D) and four sensors (i.e. 1, 2, 3, and 4) are illustrated above, the number of target VOCs and the number of VOC sensors present in the analysis may vary from application to application, or from use to use, and is not only limited to four. As a result, the problem of determining concentrations for several target VOCs and/or background and interferent gases present within a certain fluid flow becomes possible.

In some embodiments, the method 200 may further comprise operating a user interface to communicate the results of the analysis (S242). That is, the device provided in step S204 may further comprise a user interface configured to display the results of the analysis of the target fluid flow to an associated user. For example, the user interface may be configured to display or otherwise indicate the presence of an insect infestation, including the presence of one or more insects (e.g. SPIs). The presence of an infestation by be indicated based on a pre-determined threshold concentrations, which may be associated with the type of storage facility (e.g. within a trailer, land/sea container, bulk tote, pallet of bagged ingredients or a storage room) or the type of stored product being tested. The user interface may further be configured to display or otherwise indicate the level of the presence of insects based on the detected target VOCs (e.g. the degree of infestation).

In particular embodiments, the user interface may be a dedicated screen, such as a TFT LCD screen, an IPS LCD screen, a capacitive touchscreen LCD, an LED screen, an OLED screen, an AMOLED screen, or the like. In further embodiments, the user interface may comprise a wired or wireless communications protocol, such as Bluetooth, BLE, Wi-Fi, 3G, 4G, 5G, LTE, or the like, and the user interface may be configured to communicate the results of the analysis to a secondary device (e.g. a mobile phone, tablet, computer, etc.) of the associated user via the communication protocol.

In preferred embodiments, the target fluid flow is an air sample (or volume) taken from within a proximity to the stored product being evaluated for possible insect infestation. In a step S244, the steps S232 to S242 may be repeated by sampling a plurality of target fluid flows (e.g. air samples) from within a plurality of proximities to the stored product(s) being evaluated. That is, the method 200 may also include identify a source of insect infestation, for example, by detecting a gradient of target VOCs over two or more target fluid flows (e.g. a first target fluid flow, a second target fluid flow, a third target fluid flow, etc.) at varying distances from the stored product(s).

In further embodiments of the method 200, the device provided in step S204 may also comprise a controller operatively connected to the sensor array and the user interface, wherein the controller includes a processor that is configured to perform one or more steps of the method 200 described above, and a memory configured to store one or more of the data types discussed above. Furthermore, the memory may be configured to store instructions for performing one or more of the steps of the method 200.

At a step S250, the method 200 may end.

These and other aspects of devices used to implement the methods 100, 200 described herein may be understood more readily by reference to discussion below and the various drawings discussed therein.

Devices and Systems

Disclosed herein are devices and systems performing the methods 100, 200 described above. In particular, discussed herein are highly sensitive and highly selective devices for detecting one or more target volatile organic compounds ("VOCs"), such as certain semiochemicals, kairomones, and/or pheromones of various stored product insects ("SPIs"), within a target fluid flow. Further, the devices and systems may be compact and light enough to be easily portable and handheld.

Figure 3:
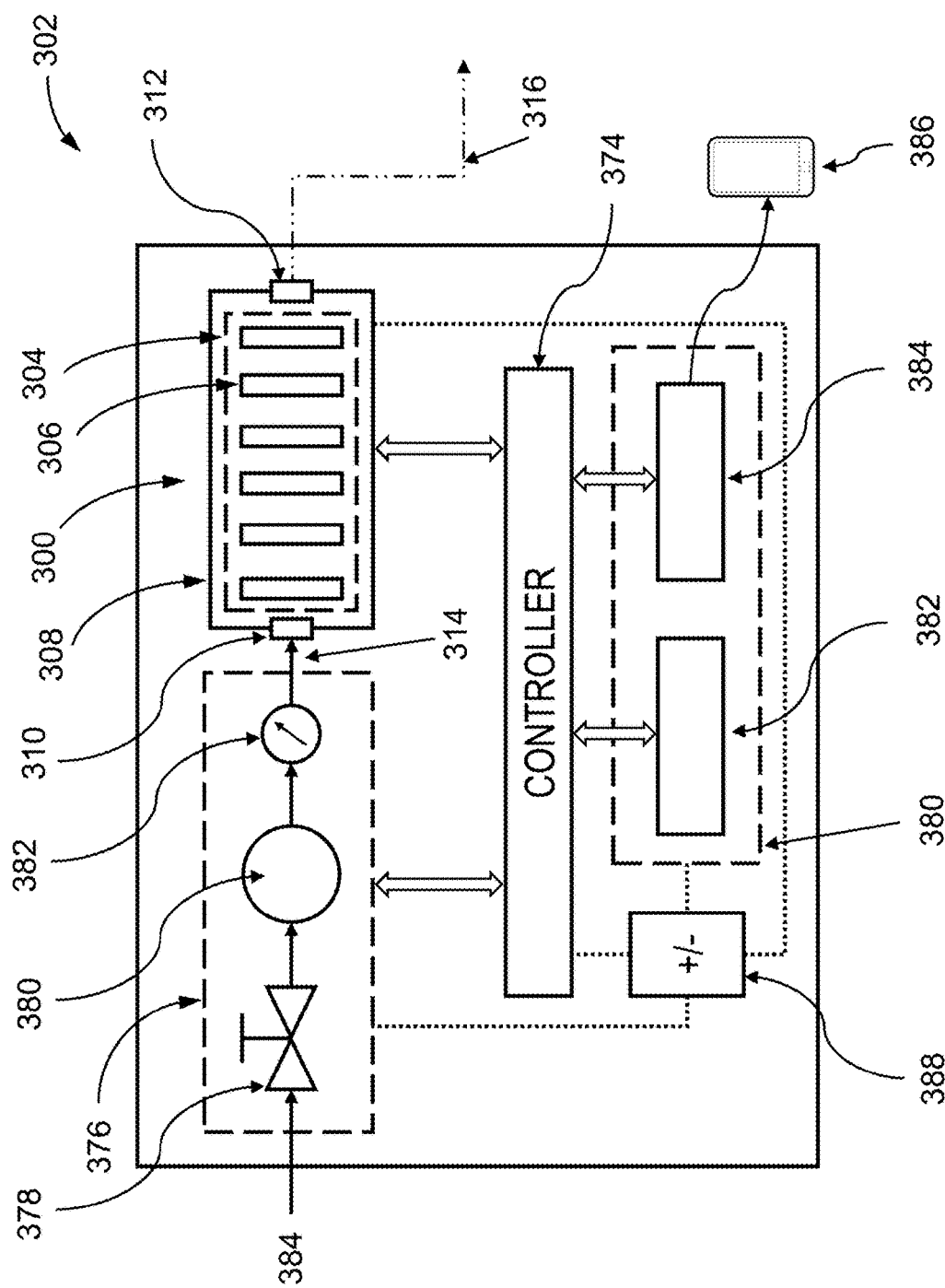
FIG. 3 is a block diagram illustrating a system configured to perform the methods disclosed herein in accordance with one embodiment of the subject application.

With reference to FIG. 3, a block diagram illustrating a device 300 and a system 302 configured to perform the methods disclosed herein in accordance with one embodiment of the subject application. In particular, the device 300 comprises a sensor array 304 having a plurality of VOC sensors 306. The plurality of VOC sensors 306 of the sensor array 304 may comprise from about two to about ten VOC sensors, including three, four, five, and six VOC sensors. In particular embodiments, the sensor array 304 may be enclosed in a chamber (or reactor) 308, wherein the sensors 306 are exposed to (i.e. come into contact with) a desired atmosphere within the chamber 308. The chamber may have an inlet 310 configured to receive a fluid flow 314 from outside the chamber, and an outlet 312 configured to relieve the chamber 308 of a fluid flow 316.

Figure 4:
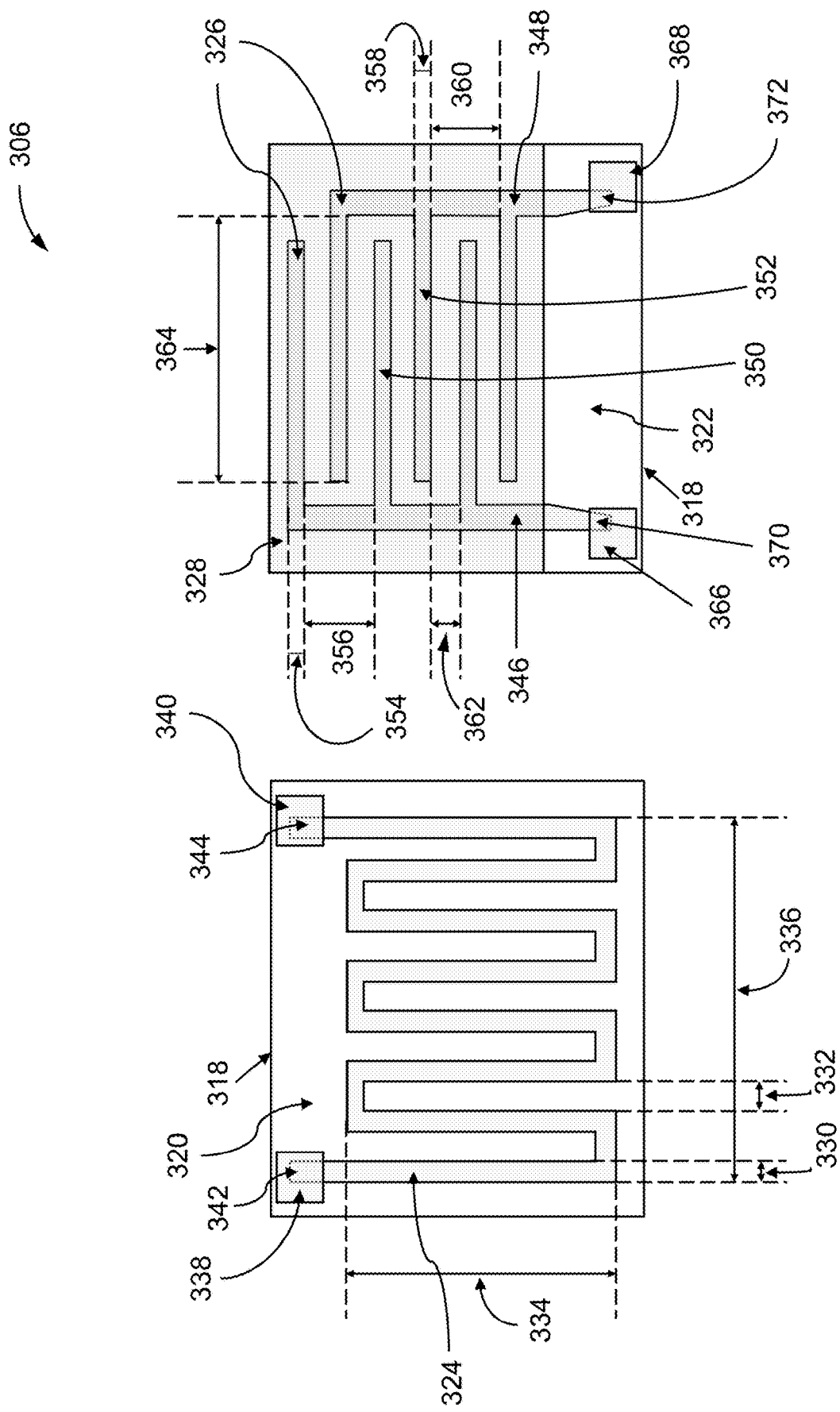
FIGS. 4A-4B are an illustration of a first side (FIG. 4A) and a second side (FIG. 4B) of an individual VOC sensor in accordance with certain embodiments of the subject application.

As shown in FIG. 4A and FIG. 4B, which illustrates a first side (FIG. 4A) and a second side (FIG. 4B) of an individual VOC sensor 306 of a sensor array 304, the VOC sensor 306 can comprise a substrate 318 having a first side 320 and a second side 322. The substrate 318 can be, for example, a ceramic material, or may be an alumina ($Al_2O_3$) wafer or a silicon wafer. In particular embodiments, the substrate 318 may have an overall width of about 5 mm to about 20 mm, an overall height of about 4.3 mm to about 20 mm, and an overall thickness of about 0.32 mm to about 0.65 mm. The VOC sensor 306 may include a resistive heater circuit formed on the first side 320 of the substrate 318, a sensing circuit 326 formed on the second side 322 of the substrate 318, and a chemically sensitive film 328 formed over the sensing circuit 326 on the second side 322 of the substrate 318.

The resistive heater circuit 324 may be formed on the substrate 318 from a heater circuit material using, for example, photolithography. In some embodiments, the heater circuit material may comprise platinum. In particular embodiments, the heater circuit material may be platinum ink comprising from about 70 wt % to about 95 wt % platinum.

The heater circuit material can be, for example, photolithographed on the substrate 318 into a desirable pattern. In particular embodiments, the resistive heater circuit 324 of at least one of the plurality of VOC sensors 306 of the sensor array 304 may have a serpentine (i.e. winding) pattern across a portion of the substrate 318. For example, in some embodiments, the resistive heater circuit 324 can have a longitudinal trace width 330 of from about 0.288 mm to about 0.352 mm. In further embodiments, the resistive heater circuit 324 can have a longitudinal trace spacing 332 of from about 0.333 mm to about 0.407 mm, for example. In still further embodiments, at least a portion of the resistive heater circuit 324 may have a trace height 334 of about 3.80 mm to about 3.96 mm, an outer trace width 336 of about 4.40 mm to about 4.58 mm, and a trace thickness (i.e. depth) of about 0.19 mm to about 0.24 mm, including about 0.21 mm.

The first side 320 of the VOC sensor 306 substrate 318 may also include one or more terminals 338, 340. For example, as shown in FIG. 4A, the first side 320 of substrate 318 includes at least two terminals 338, 340, which are each operatively connected to a portion (e.g. opposite ends) 342, 344 of the resistive heater circuit 324.

Turning now to FIG. 4B, the sensing circuit 326 may be formed on the substrate 318 from a sensing circuit material using, for example, photolithography. In some embodiments, the sensing circuit material may comprise platinum. In particular embodiments, the sensing circuit material may comprise a platinum ink having from about 70 wt % to about 95 wt % platinum.

The sensing circuit material can be, for example, photolithographed on the substrate 318 into a desirable pattern. In particular embodiments, the sensing circuit 326 includes a first sensing element 346 and a second sensing element 348 that form a pair of extended inter-digitated contacts (i.e. alternating, un-connected contacts in close proximity). The first sensing element 346 may comprise a plurality of extended contacts 350, wherein each contact 350 has a latitudinal trace width 354 of from about 0.162 mm to about 0.198 mm, a latitudinal trace spacing 356 of from about 0.738 mm to about 0.902 mm, and a trace thickness (i.e. depth) of about 0.19 mm to about 0.24 mm. For example, the contacts 350 may have a latitudinal trace width 354 of about 0.18 mm, a latitudinal trace spacing 356 of about 0.82 mm, and a trace thickness of about 0.21 mm.

Similarly, the second sensing element 348 may comprise a plurality of extended contacts 352, wherein each contact 352 has a latitudinal trace width 358 of from about 0.162 mm to about 0.198 mm, a latitudinal trace spacing 360 of from about 0.738 mm to about 0.902 mm, and a trace thickness (i.e. depth) of about 0.19 mm to about 0.24 mm. For example, the contacts 354 may have a latitudinal trace width 358 of about 0.18 mm, a latitudinal trace spacing 360 of about 0.82 mm, and a trace thickness of about 0.21 mm.

In some embodiments, each of the first and second sensing elements 346, 348 may include at least three contacts 350, 352, and have a latitudinal trace spacing 362 between each contact 350, 352 of the first and second sensing elements 346, 348 of from about 0.288 mm to about 0.352 mm, including about 0.32 mm. Further, each of the contacts 350, 352 may have a longitudinal trace length 364 of about 3.0 mm to about 4.0 mm, including about 3.8 mm.

The second side 322 of the substrate 318 may also comprise one or more terminals 366, 368 which may be operatively connected to a portion 370, 372 of the sensing circuit 326.

Additionally, the contacts 350, 352 of the sensing circuit 326 may be over-coated with a coating composition to form the chemically-sensitive film 328. In some embodiments, the coating composition may comprise a gel, and the film 328 may be formed by applying the coating composition to a portion of the substrate 318 (e.g. a portion covering the contacts 350, 352), and then drying and calcining the coating composition at a high temperature such as, for example, from about 400° C. to about 900° C., including from about 500° C. to about 700° C.

In particular embodiments, the film 328 may be a metal oxide film, such as a tin oxide ($SnO_2$) semiconductor film. In such embodiments, the coating composition can comprise tin oxide produced using a water-based gel. In certain embodiments, the gel is made by a sol-gel process involving $SnCl4$ to form an acidic tin solution, which is neutralized to produce a $SnO_2$ gel. A nano-crystalline $SnO_2$ film 328 is then formed on the substrate 318, for example, by spin coating the aqueous $SnO_2$ gel onto the sensor side 322 of the substrate 318, drying the sensor 306 at a first temperature, and then calcining at a second temperature. In particular embodiments, the first temperature at which drying occurs is from about 100° C. to about 150° C., and may preferably be about 130° C. In further embodiments, the second temperature at which calcining occurs is from about 400° C. to about 900° C., and may preferably be from about 700° C. to about 800° C. Importantly, these temperature ranges create a pore size distribution and particle size distribution that provides excellent sensitivity in the chemically-sensitive films 328.

Due to the chemical structures of the target VOCs and the operating conditions of each of the VOC sensors 306, when the target VOCs (e.g. marker gases) come into contact with the chemically-sensitive film 328, the number of electrons available in the conduction band of the film 328 may be affected (i.e. increased or decreased). In particular embodiments, the one or more of the target VOCs may be a "reducing gas", which donate additional electrons to the film's 328 conduction band, thereby reducing the resistance of film 328, which may then be measured as a change in conductance of the film 328. Certain target pheromones, semiochemicals, and kairomones may comprise a six-membered carbon ring and one or more carbonyl groups (—C=O). This is the region of the molecule in which excess electron density is located, which allows for interaction with the semiconductor film 328, contributing charge carriers to the conduction band of the film 328 (i.e. decreasing the resistance of the film 328). The chemical structures for two semiochemicals are shown below in Table 3:

TABLE 3

Semiochemical/Kairomone Chemical Structures

| SPI | Chemical Formula | Chemical Structure |
| --- | --- | --- |
| Indian meal moth larvae *Plodia interpunctella* | 2-palmitoyl-1,3-cyclohexanedione | 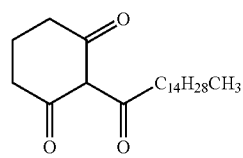 |
| Indian meal moth larvae *Plodia interpunctella* | 2-oleoyl-1,3-cyclohexanedione | 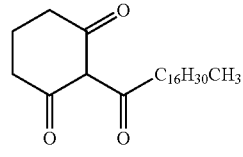 |

In preferred embodiments, the sensor array 304 includes a plurality of differentiated VOC sensors 306. That is, the composition of one or more of the plurality of VOC sensors 306 are varied and optimized for specific detection needs. For example, the coating composition used to form the film 328 may include one or more catalysts or dopants (e.g.

doping agents), which may be added while the gel coating composition is being made. In some embodiments, the coating composition including a doping agent. In some embodiments, the doping agent may be, for example, a transition metal. For example, the doping agent may be selected from a group consisting of: platinum; palladium; molybdenum; tungsten; nickel; ruthenium; and osmium. As a result of the addition of a doping agent to a film 328 of a VOC sensor 306, each VOC sensor 306 may be optimized for a given gas or target VOC. In particular embodiments, the device 300 may include a plurality of VOC sensors 306 wherein at least one of the VOC sensors 306 is optimized for a particular gas or target VOC by the addition of a catalyst or dopant (i.e. doping agent). In further embodiments, each of the VOC sensors 306 present in the device 300 is optimized for a particular gas or target VOC by the addition of a catalyst or dopant (i.e. doping agent). For example, in specific embodiments, a sensor array 304 may include a first VOC sensor 306 optimized for IMM larvae semiochemicals, a second VOC sensor 306 optimized for an adult IMM pheromone, and up to three VOC sensors 306 optimized for potential interferent and/or background gases; however, other combinations and quantities of VOC sensors 306 are contemplated. Potential interferent and/or background gases may comprise, for example, hydrocarbons, alcohols, esters, and/or aldehydes.

Figure 5:
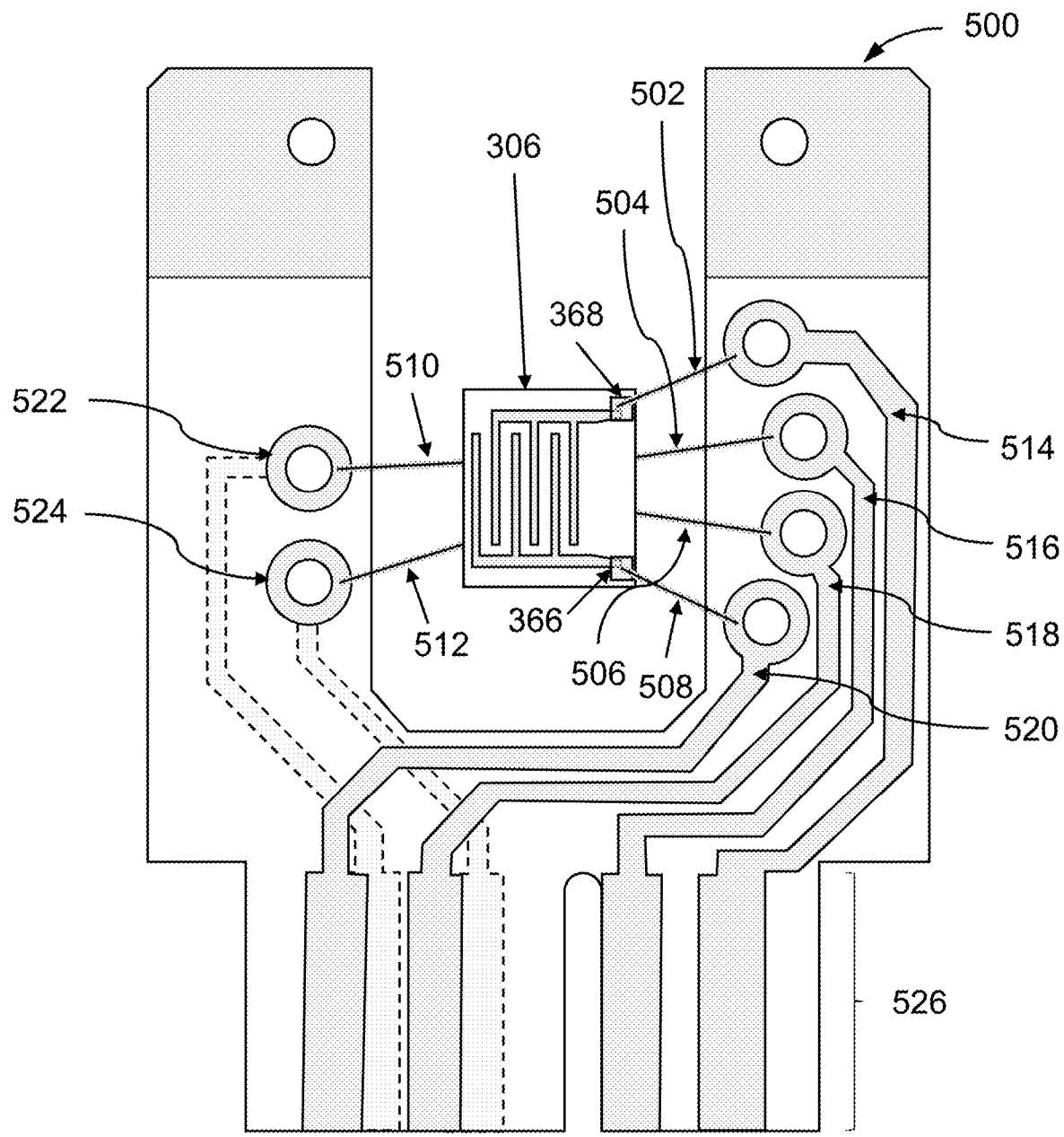
FIG. 5 is an illustration of an individual VOC sensor suspended in a holder in accordance with one embodiment of the subject application.

Each of the VOC sensors 306 of the device 300 may be positioned within the chamber 308 such that the chemically sensitive film 328 is able to be exposed to a fluid flow that enters the chamber 308. With reference to FIG. 5, in particular embodiments, each of the VOC sensors 306 may be suspended, for example, in a holder 500 using wire bonding 502, 504, 506, 50, 510, 512 to hold up the sensor 306 and to connect various sensor 306 terminals 340, 342, 366, 368 to contacts 514, 516, 518, 520, 522, 524 of the sensor holder 500.

Figure 6:
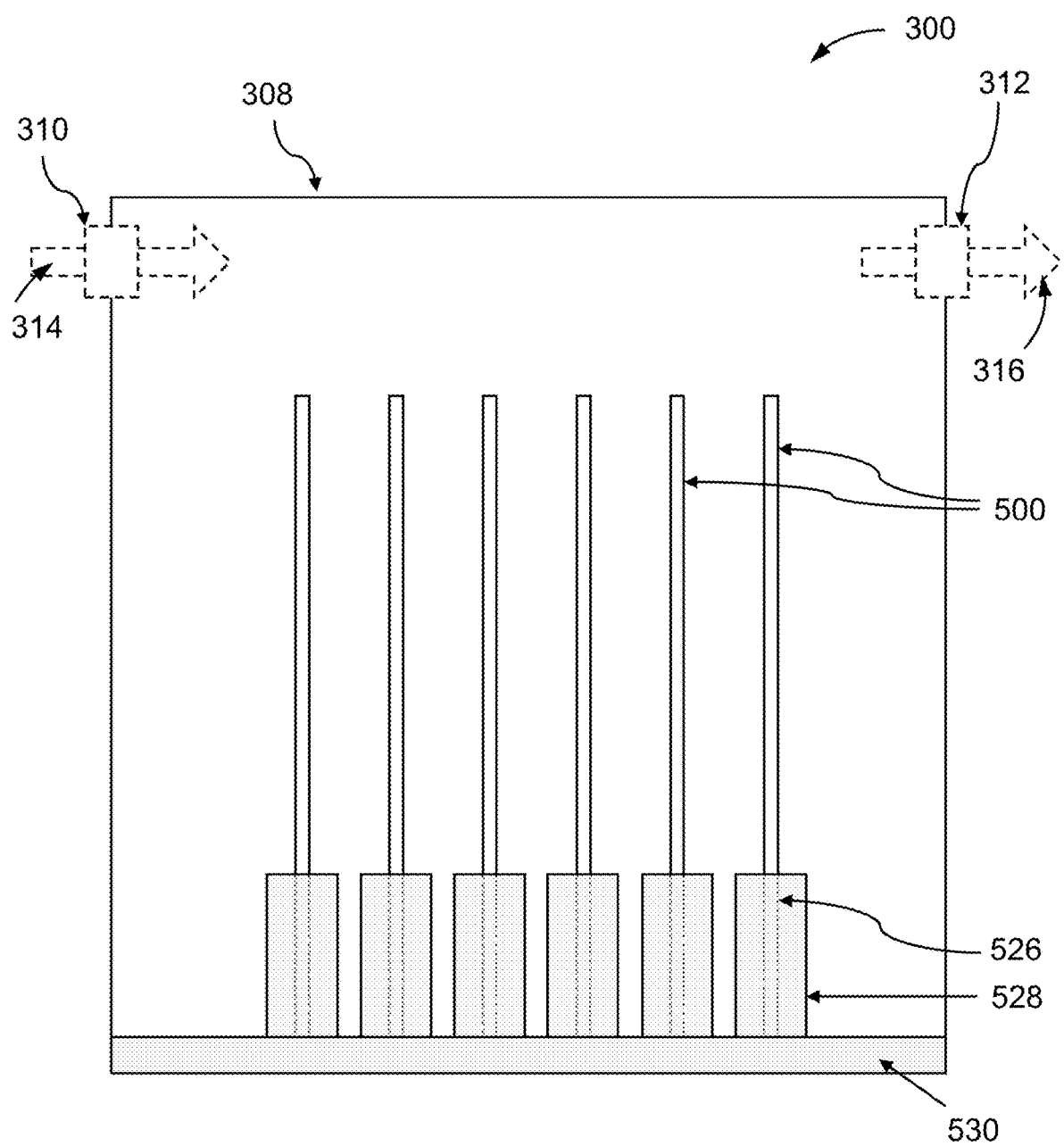
FIG. 6 is a representative side-view cross-section of a sensor array comprising a plurality of VOC sensors in accordance with one embodiment of the subject application.

With further reference to FIG. 6, a side view of the device 300 is shown in accordance with certain aspects of this disclosure. In particular, the device 300 illustrates a sensor array 304 comprising six VOC sensors 306 (not visible) being suspended within a chamber 308 by sensor holders 500. Further, in accordance with some embodiments, a portion 526 of each of the sensor holders 500 may operatively engage an adapter 528 operatively connecting holders 500 and VOC sensors 306 to a circuit board 530 of the device 300, which allows for power to be supplied to the VOC sensors 306 and for measurements to be taken, for instance.

In other words, the sensor array 304 may be operatively connected to a controller 374 configured to perform one or more steps of the methods described above. In particular, the controller 374 may be configured to: heat one or more of the plurality of VOC sensors 306 to at least a first operating temperature; measure the conductance of one or more of the plurality of VOC sensors 306; determine a set of conductance change values corresponding to each of the one or more VOC sensors 306 contacted with a fluid flow; and determine a gas component concentration for one or more of the target VOCs within the fluid flow based on the set of conductance change values.

Returning to FIG. 3, additional components of the infestation detection system 302 are described in accordance with various aspects of the subject application. A system 302 is provided for identifying an insect infestation of a stored product, the system 302 comprising the sensor array 304 as previously described. Further, in particular embodiments, the system 302 includes a testing chamber 308 enclosing the sensor array 304, an air transfer unit 376, and a controller 374 operatively connected to the air transfer unit 376 and the sensor array 304.

The air transfer unit 376 can comprise, in various embodiments, a valve 378 for controlling the fluid flow through the system 302, a pump 380 for retrieving (or drawing in) a fluid flow from outside the system 302 and for delivering (or pushing) the fluid flow through the system 302, and a fluid flow sensor 382 for measuring the amount (e.g. a volume) of fluid that is retrieved by the air transfer unit 376. In particular embodiments, the fluid flow sensor 382 may be a mass flow control valve or a differential pressure transducer. In further embodiments, the valve 378 and pump 380 may be user actuated. That is, an associated operator of the system 302 may direct (e.g. physically trigger) the retrieval of an external fluid flow using the air transfer unit 376.

The air transfer unit 302 may also define a fluid flow path of a fluid flow 384 from outside the system 302, to a flow 314 into the inlet 310 of the device 300, and to a flow 316 exiting the outlet 312 of the device 300. Portions of the fluid flows 314, 316, 384 may be transmitted along a fluid flow carrier, such as polymer tubing.

Additionally, the air transfer unit 376 can be operatively connected to the controller 374, such that the controller 374 may operate the air transfer unit 376 to retrieve a fluid flow from and deliver the fluid flow to the chamber 308, where the fluid flow can be in fluid contact with the VOC sensors 306. In particular embodiments, the controller 374 may, for example, measure the amount (e.g. volume) of the fluid flow entering the system 302 and instruct the air transfer unit 376 (e.g. the pump 380 and/or valve 378) to stop drawing in fluid (e.g. air) once the measured amount reaches a pre-determined threshold. In some embodiments, the pre-determined threshold is a volume sufficient for the device 300 to detect and measure the presence of one or more target VOCs in the fluid flow.

The controller 374 of the system 302 can be operatively connected to the air transfer unit 376 and the sensor array 304, and may comprise a processor and a memory. The controller 374 may be further configured to: operate the air transfer unit 376 to retrieve a fluid flow (e.g. fluid flow 378) from outside the system 302 and deliver the fluid flow (e.g. fluid flow 314) to the testing chamber 308, wherein the plurality of VOC sensors 306 are in fluid contact with the fluid flow 314; operate the sensor array 304 to heat one or more VOC sensors 306 to at least a first operating temperature and measure the conductance for one or more of the plurality of VOC sensors 306; determine a set of conductance change values corresponding to each of the one or more VOC sensors 306; and determine a gas component concentration for one or more target VOCs within the fluid flow 314 based on the set of conductance change values.

In some embodiments, the system 302 further includes a user interface component(s) 380. The user interface 380 may be operatively connected to the controller 374, and the controller 374 can be configured to operate the user interface 380 to display and/or communicate the results of the testing performed via the system 302 to an associated user. The user interface 380 may be a dedicated display 382 visible to a user or operator of the system 302, such as a display comprising a TFT LCD screen, an IPS LCD screen, a capacitive touchscreen LCD, an LED screen, an OLED screen, an AMOLED screen, or the like. In further embodiments, the user interface 380 may comprise a wired or wireless communications protocol 384, such as Bluetooth, BLE, Wi-Fi, 3G, 4G, 5G, LTE, or the like, and the user interface 380 may be configured to communicate the results of the analysis to a secondary device 386 (e.g. a mobile phone, tablet, computer, etc.) of an associated user via the communication protocol.

The system 302 may also comprise a power supply 388 that is operatively connected to at least one of the air transfer unit 376, the device 300, the controller 374, and the user interface 380. The power supply 388 may be configured to deliver power to one or more of the components of the system 302, while the controller 374 can be configured to operate the power supply 388. In particular embodiments, the power supply 388 may be integrated into the system 302. In further embodiments, the power supply 388 may be a removable, external accessory. In some embodiments, the power supply 388 may be a rechargeable power supply 388.

Figure 7:
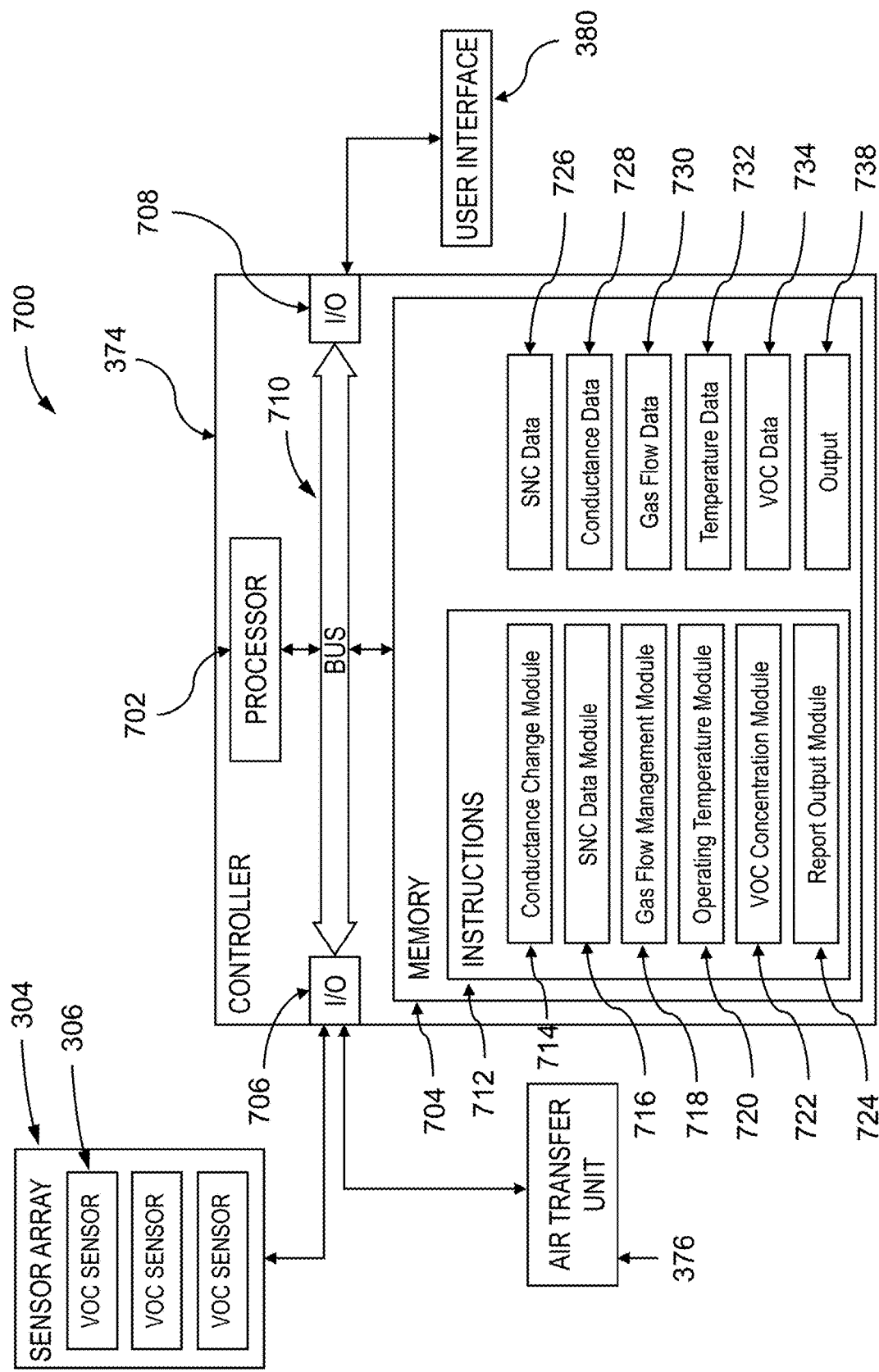
FIG. 7 is a block diagram of an infestation detection system in accordance with one embodiment of the subject application.

The various components of the systems described are now discussed in more detail with reference to FIG. 7. As shown, FIG. 7 illustrates a block diagram of a system 700 for identifying an insect infestation of a stored product by, for example, detecting presence and measuring the level of one or more target VOCs. The system 700 includes a sensory array 306 comprising a controller 374 having a processor 702, a memory 704, and one or more input/output (I/O) interfaces 706, 708. A bus 710 may operatively connect the processor 702, memory 704, and the I/O interfaces 706, 708 together. The memory 704 includes instructions 712 for performing one or more steps of the methods disclosed herein, and the processor 702, in communication with the memory 704, is configured to execute the instructions for performing the one or more steps.

As illustrated, the system 700 may also include a sensor array 304 comprising a plurality of VOC sensors 306, as well as an air transfer unit 376 and a user interface 380. The processor 702 may also control the overall operation of the system 700, including the operation of the sensor array 304, the air transfer unit 376, and the user interface 380.

The memory 704 may represent any type of non-transitory computer readable medium such as random access memory (RAM), read only memory (ROM), magnetic disk or tape, optical disk, flash memory, or holographic memory. In one embodiment, the memory 704 comprises a combination of random access memory and read only memory. In some embodiments, the processor 702 and memory 704 may be combined in a single chip. The input/output (I/O) interfaces 706, 708 allow the controller 374 to communicate with other components of the system 700, such as the sensor array 304, the fluid flow sensor 382, the air transfer unit 376, and the user interface 380, via wired or wireless connections. The digital processor 702 can be variously embodied, such as by a single-core processor, a dual-core processor (or more generally by a multiple-core processor), a digital processor, and cooperating method coprocessor, a digital controller, or the like.

The term "software," as used herein, is intended to encompass any collection or set of instructions executable by a computer or other digital system so as to configure the computer or other digital system to perform the task that is the intent of the software. The term "software" is intended to encompass such instructions stored in storage mediums such as RAM, a hard disk, optical disk, or so forth, and is also intended to encompass so-called "firmware" that is software stored on a ROM or so forth. Such software may be organized in various ways, and may include software components organized as libraries, Internet-based programs stored on a remote server or so forth, source code, interpretive code, object code, directly executable code, and so forth. It is contemplated that the software may invoke system-level code or calls to other software residing on a server or other location to perform certain functions.

The instructions 712 of the controller 374 can include in various embodiments a conductance change module 714, a specific net conductance ("SNC") data module 716, a gas flow management module 718, an operating temperature module 720, a VOC concentration module 722, and a report output module 724, for example.

The conductance change module 714 can be configured to measure the conductance of one or more VOC sensors 306 of the sensor array 304 and record the conductance data 728 in memory 704. That is, in particular embodiments, the conductance change module 714 can be configured to instruct the processor 702 to measure the bulk resistance change of the chemically-sensitive film 328 of the one or more VOC sensors 306 using the respective sensing circuits 326. Thus, the conductance change module 714 may be configured to measure and receive, via I/O interface 706, conductance signals from the VOC sensors 306 of the sensor array 304, and store the conductances in the memory 306 as conductance data 728. The conductance change module 714 may also be configured to, for example, minimize electronic noise and drift of the conductance signals measured from the VOC sensors 306 to ensure accurate and precise measurements. In some embodiments, the conductance change module 714 may be configured to apply, for example, a signal model and/or algorithm to manage or eliminate the problems of conductance drift and electronic noise in the measurement of sensor conductance. In further embodiments, the conductance change module 714 may be configured to adjust the conductance values of the one or more VOC sensors by measuring the conductance of the VOC sensors and raising and/or lowering the operating temperature of one or more of the VOC sensors (via the operating temperature module 720) until the conductance value for a VOC sensor matches a previously determined baseline conductance value.

The SNC data module 716 can be configured to determine the specific net conductance ("SNC") of one or more of the VOC sensors 306 of the sensor array 304, as described previously. In particular, the SNC data module 716 and the conductance change module 714 may operate to measure and receive, via I/O interface 706, certain conductance signals (e.g. conductance values of the VOC sensors contacted with a control fluid flow and/or a sample fluid flow absent target VOCs). Then, the SNC data module may determine a set of SNC values for the VOC sensors 306, and store the set of SNC values as SNC data 726 in the memory 704.

The gas flow management module 718 can be configured to operate the air transfer unit 326 to retrieve a fluid flow (e.g. fluid flow 384), deliver the fluid flow to the device 300, and purge the fluid flow (e.g. fluid flow 316) from the system 302. In particular, the gas flow management module 718 may be configured to receive, via I/O interface 706, gas flow data 730 from the fluid flow sensor 382 of the air transfer unit 376. For example, the gas flow data 730 may include a fluid intake threshold (e.g. volume) and measurements from the flow sensor 382, which may be stored in memory 704. Additionally, the gas flow management module 718 may be configured to operate the air transfer unit 376, including the valve 378 and pump 380, as well as the inlet 310 and outlet 312 controlling the fluid flow path through the system 302.

The operating temperature module 720 can be configured to operate the heater circuits 324 of the VOC sensors 306 of the sensor array 304 via I/O interface 706. In particular, the operating temperature module 720 may be configured to heat one or more of the VOC sensors 306 to at least a first operating temperature and a second operating temperature by instructing that power be applied to the heating circuits 324 of the VOC sensors 306. The operating temperature module 720 may further be configured to monitor the temperature of each of the VOC sensors 306 of the sensor array 304, and to adjust the power supplied to regulate the operating temperature(s) of the VOC sensors 306. The temperature module 720 may store the set-point operating temperature(s) of the VOC sensors 306, as well as the measured temperatures as temperature 732 in the memory 704.

The VOC concentration module 722 can be configured to determine a gas component concentration for one or more target VOCs in a fluid flow, as described above. One or more of the target VOCs may be in a gaseous form within the fluid flow (e.g. an air flow). In particular embodiments, one or more of the target VOCs is at least one of: a pheromone; a semiochemical; and a kairomone. In further embodiments, at least one of the one or more target VOCs within the fluid flow may be selected from a group consisting of: 4,8-dimethyldecanal; (Z,Z)-3,6-(11R)-Dodecadien-11-olide; (Z,Z)-3,6-Dodecadienolide; (Z,Z)-5,8-(11R)-Tetradecadien-13-olide; (Z)-5-Tetradecen-13-olide; (R)—(Z)-14-Methyl-8-hexadecenal; (R)-(E)-14-Methyl-8-hexadecen-al; γ-ethyl-γ-butyrolactone; (Z,E)-9,12-Tetradecadienyl acetate; (Z,E)-9,12-Tetra-decadien-1-ol; (Z,E)-9,12-Tetradecadienal; (Z)-9-Tetradecenyl acetate; (Z)-11-Hexa-decenyl acetate; (2S,3R,1'S)-2,3-Dihydro-3,5-dimethyl-2-ethyl-6(1-methyl-2-oxobutyl)-4H-pyran-4-one; (2S,3R,1'R)-2,3-Dihydro-3,5-dimethyl-2-ethyl-6(1-methyl-2-oxobutyl)-4H-pyran-4-one; (4S,6S,7S)-7-Hydroxy-4,6-dimethylnonan-3-one; (2S,3S)-2,6-Diethyl-3,5-dimethyl-3,4-dihydro-2H-pyran; 2-Palmitoyl-cyclohexane-1,3-dione; and 2-Oleoyl-cyclo-hexane-1,3-dione. However, other pheromones, semiochemicals, and kairomones are contemplated. The determined concentration for one or more of these target VOCs may be stored in the memory as VOC data 734.

The report output module 724 can be configured to develop the desired system output 738 and operate a user interface 380, via I/O interface 380, to communicate the output 738 to an associated user of the system 302. In particular embodiments, the user interface 380 may a dedicated display or may be a secondary user device (e.g. a PC, such as a desktop, a laptop, palmtop computer, portable digital assistant (PDA), server computer, cellular telephone, tablet computer, mobile devices, and the like, or a combination thereof). In some embodiments, the user interface 380 may include a speaker or speaker system. Thus, in some embodiments, the I/O interface 708 may be a wired communication interface. In other embodiments, the I/O interface 708 may comprise a wireless communication component, and communication with the user interface 380 may occur via a wireless communications protocol, such as Bluetooth, BLE, Wi-Fi, 3G, 4G, 5G, LTE, or the like.

In either case, the system output 738 may be communicated via the user interface 380 in various embodiments, such as a graph, chart, table, or data set, for example, illustrating the determined VOC data. In some embodiments, the output 738 may include an audible component, such as an audio tone, set of tones, or audible words, which may be communicated via a speaker or speaker system of the user interface 380. The audible output component may be a tone sounding at a frequency that varies based on the gas component concentration(s) of one or more of the target VOCs detected (e.g. increase frequency with higher detection levels). In particular embodiments, the output 738 comprises a determination of whether an insect infestation is likely present within a stored product. In further embodiments, the output 738 may include an estimate for probable cause of infestation (e.g. identifying one or more particular SPI based on the VOC data). In still further embodiments, the output 738 may include a recommendation for taking remedial action to protect the value of the stored product, such as fumigation.

EXAMPLES

The following specific examples describe novel aspects of the present disclosure and procedures used therein. They are intended for illustrative purposes only and should not be construed as a limitation upon the broadest aspects of the invention.

Figure 8A:
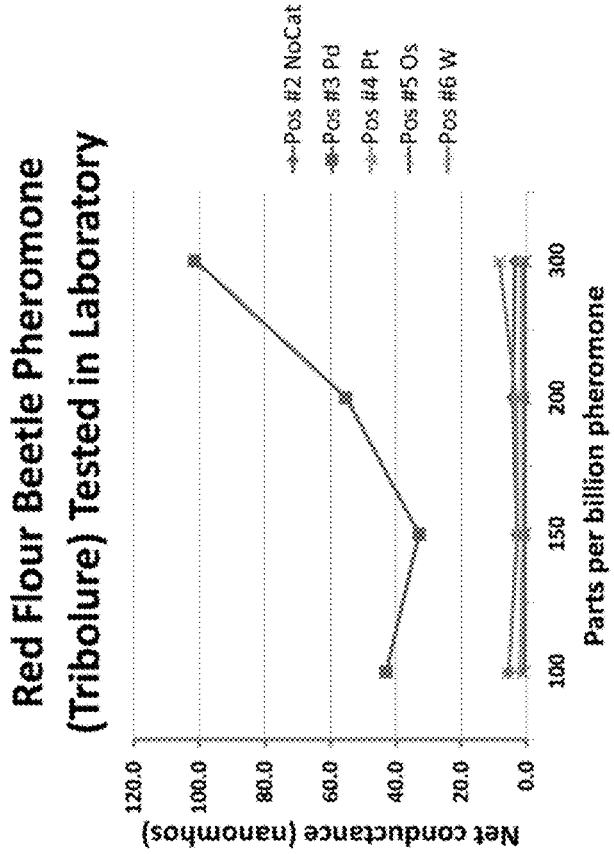
FIGS. 8A-8D are graphs illustrating the sensitivity of a VOC sensor array to various target volatile organic compounds in accordance with one embodiment of the subject application.
Figure 8B:
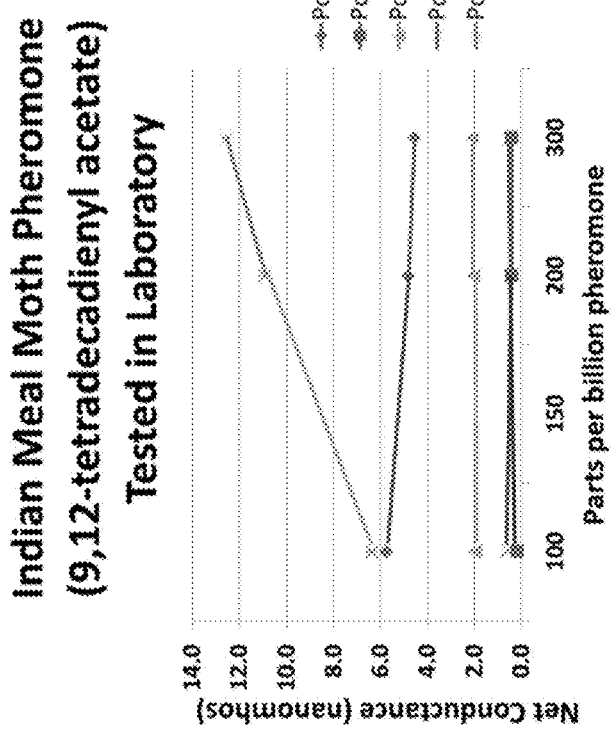
Figure 8D:
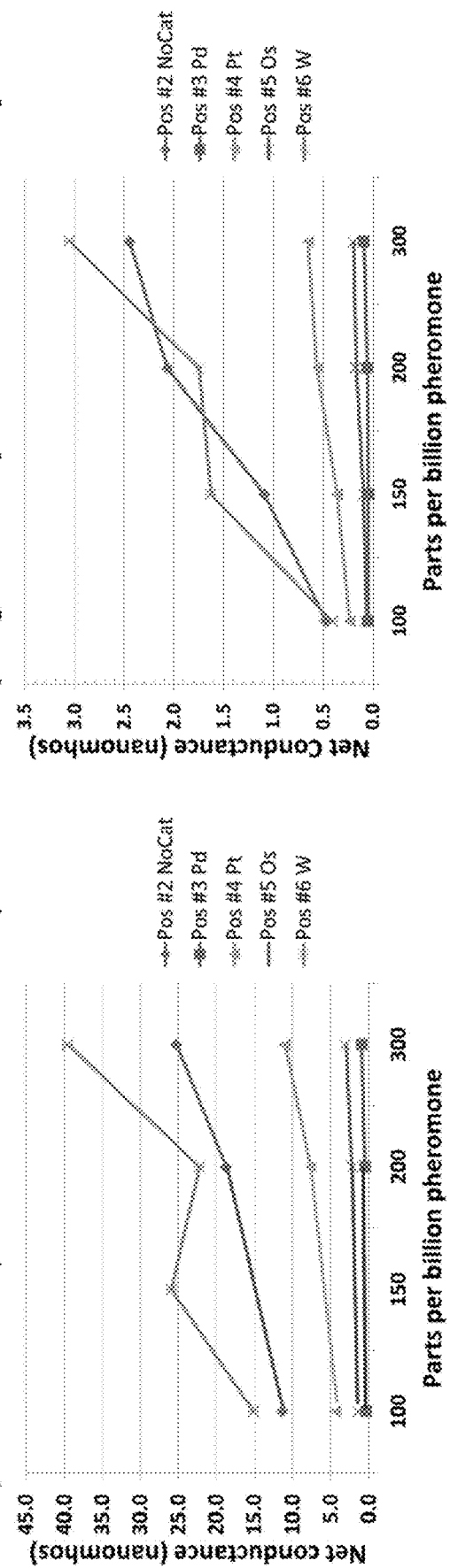
Figure 8C:
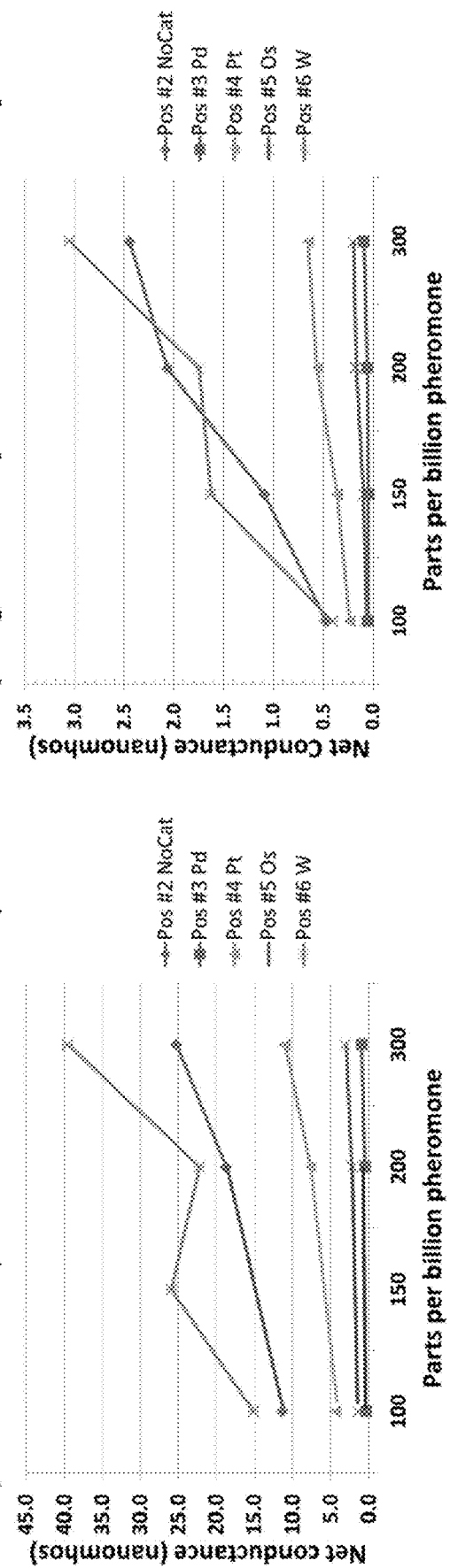
Figure 9A:
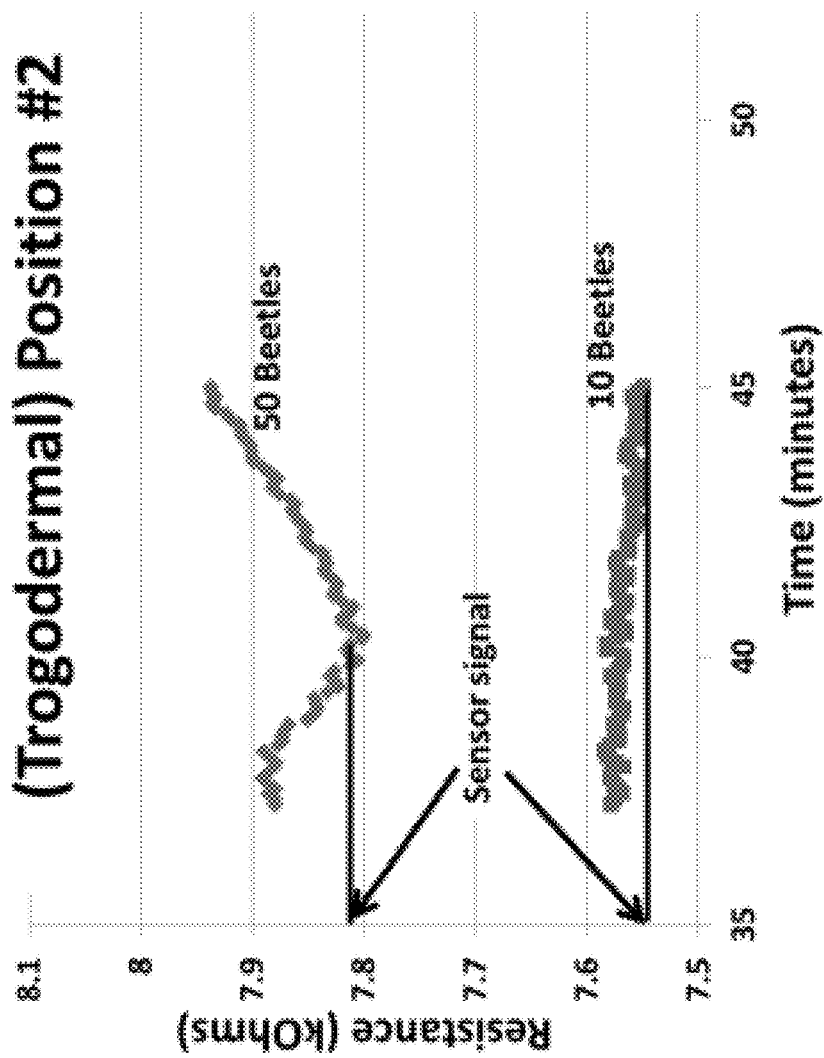
FIGS. 9A-9C are graphs illustrating the response of a first VOC sensor to the presence of three target stored product insects ("SPIs") in accordance with one embodiment of the subject application.
Figure 9B:
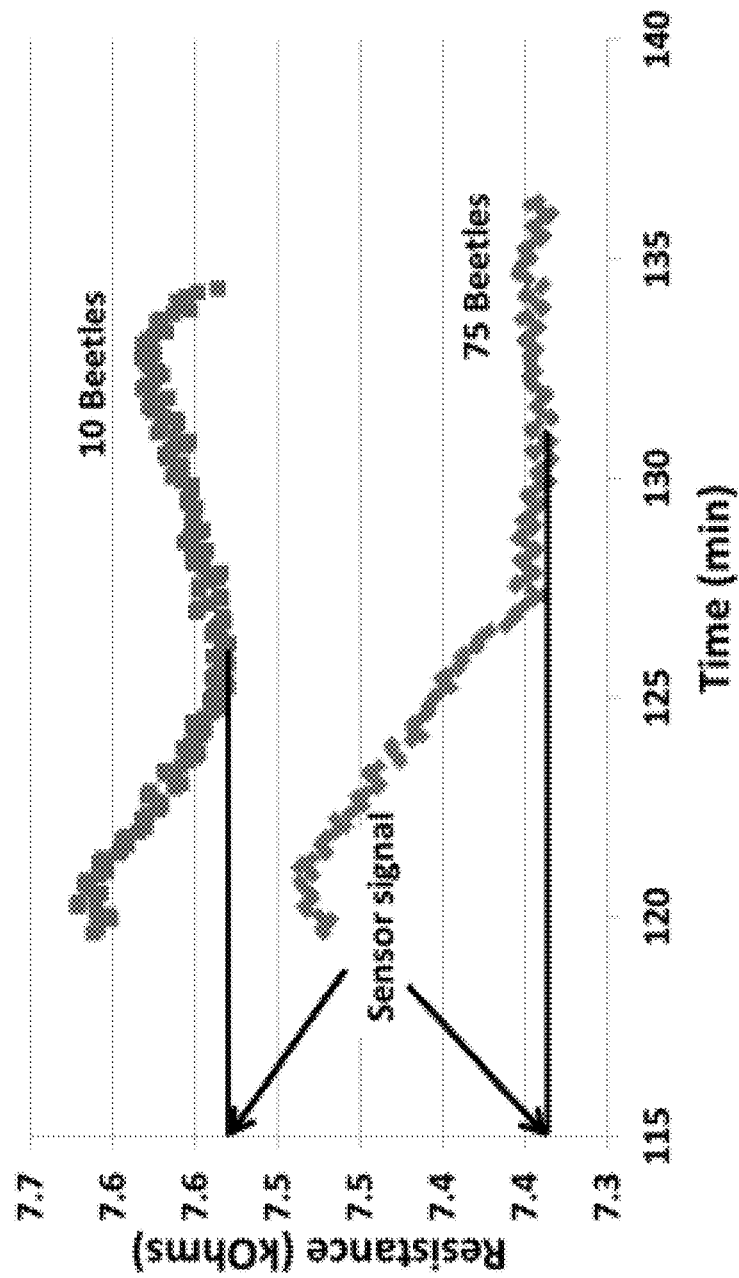
Figure 9C:
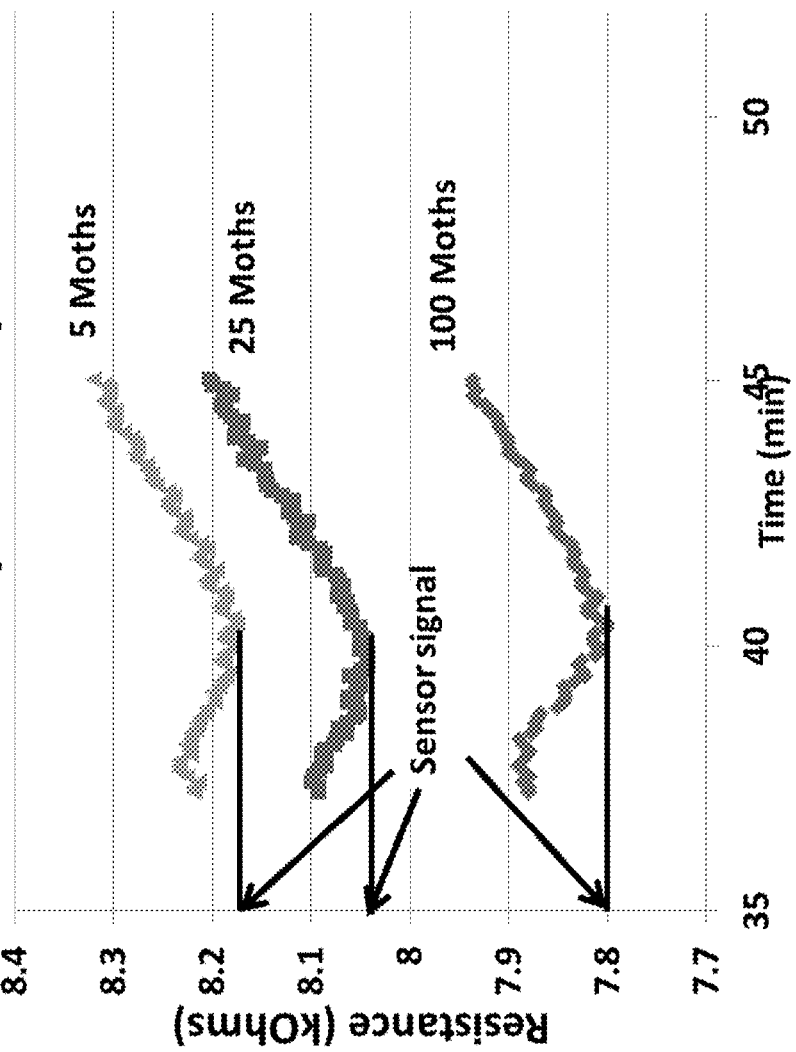
Figure 10A:
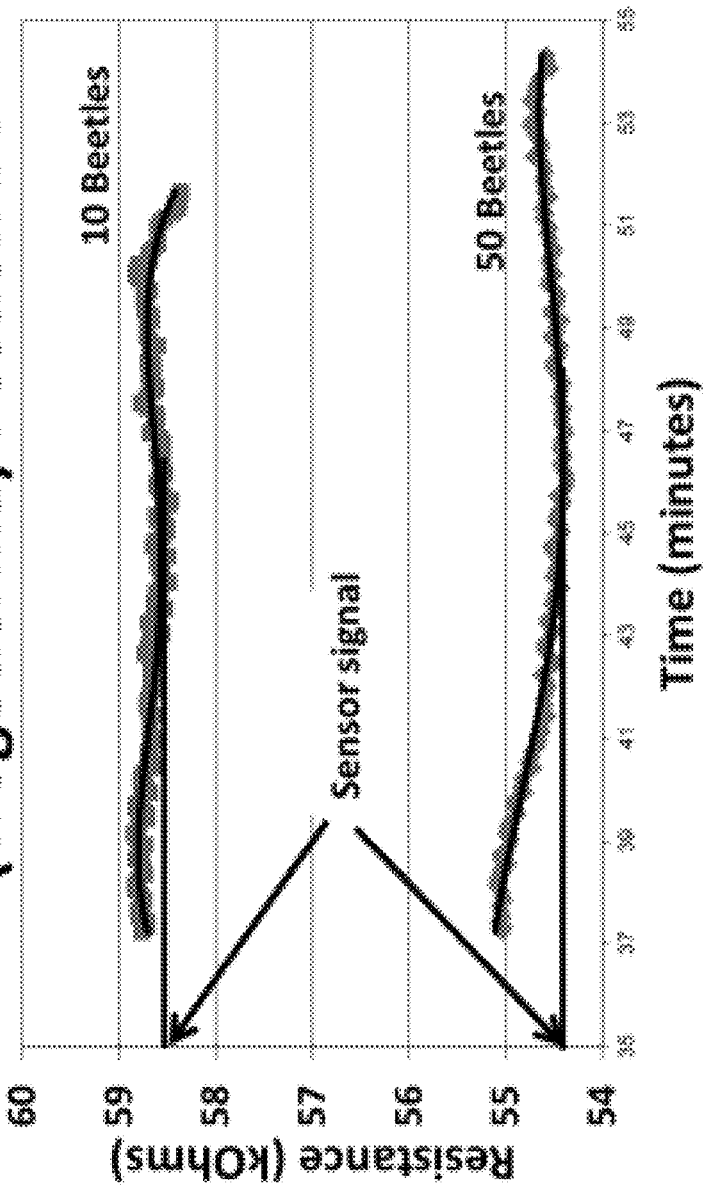
FIGS. 10A-10C are graphs illustrating the response of a second VOC sensor to the presence of three target stored product insects ("SPIs") in accordance with another embodiment of the subject application.
Figure 10B:
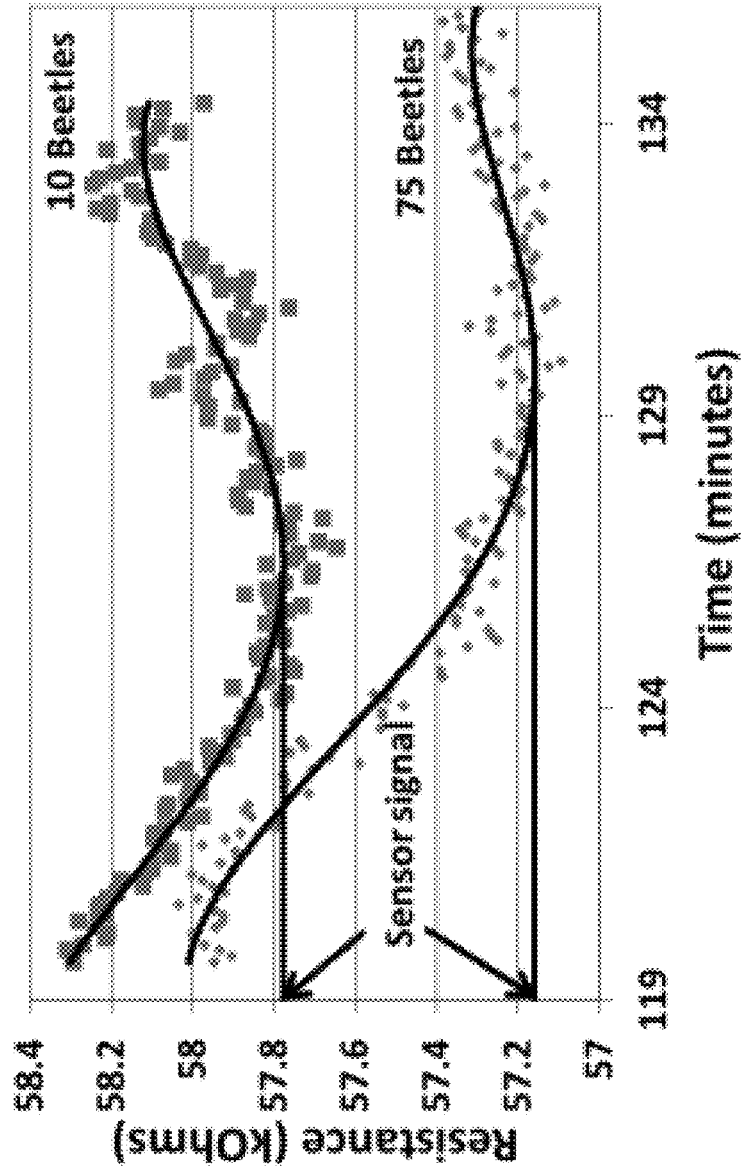
Figure 10C:
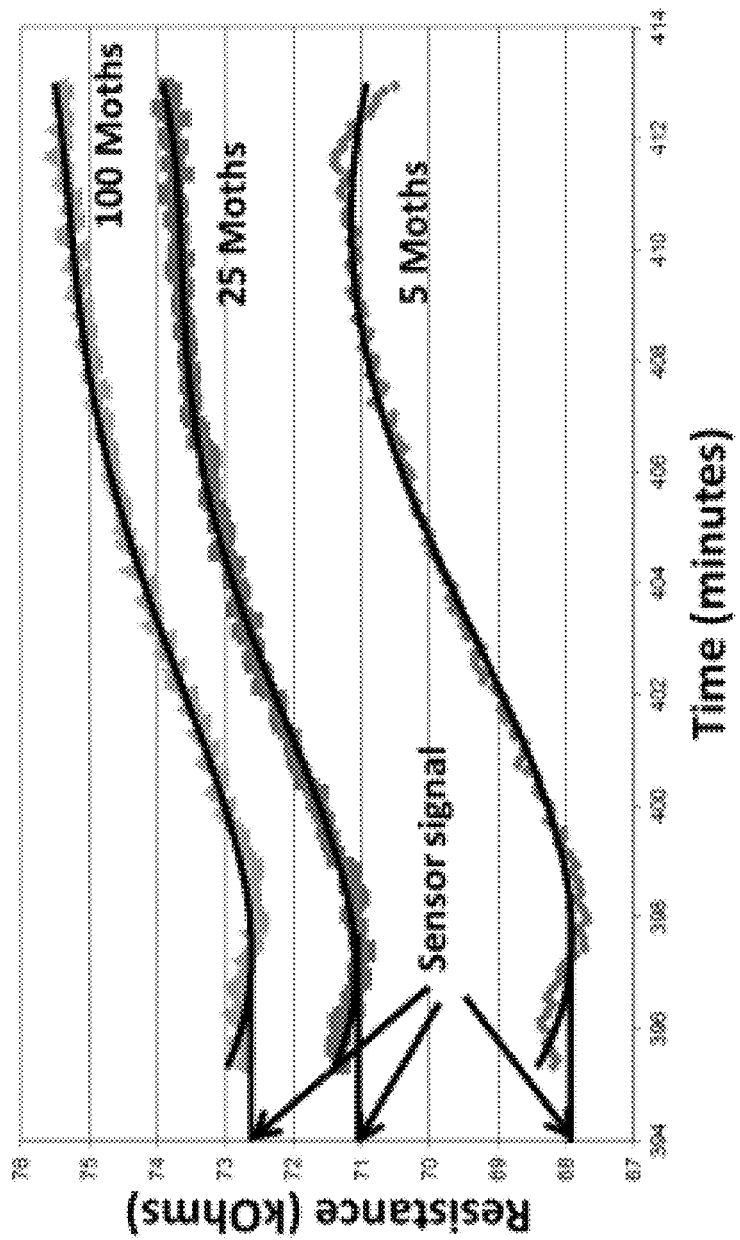
Figure 11A:
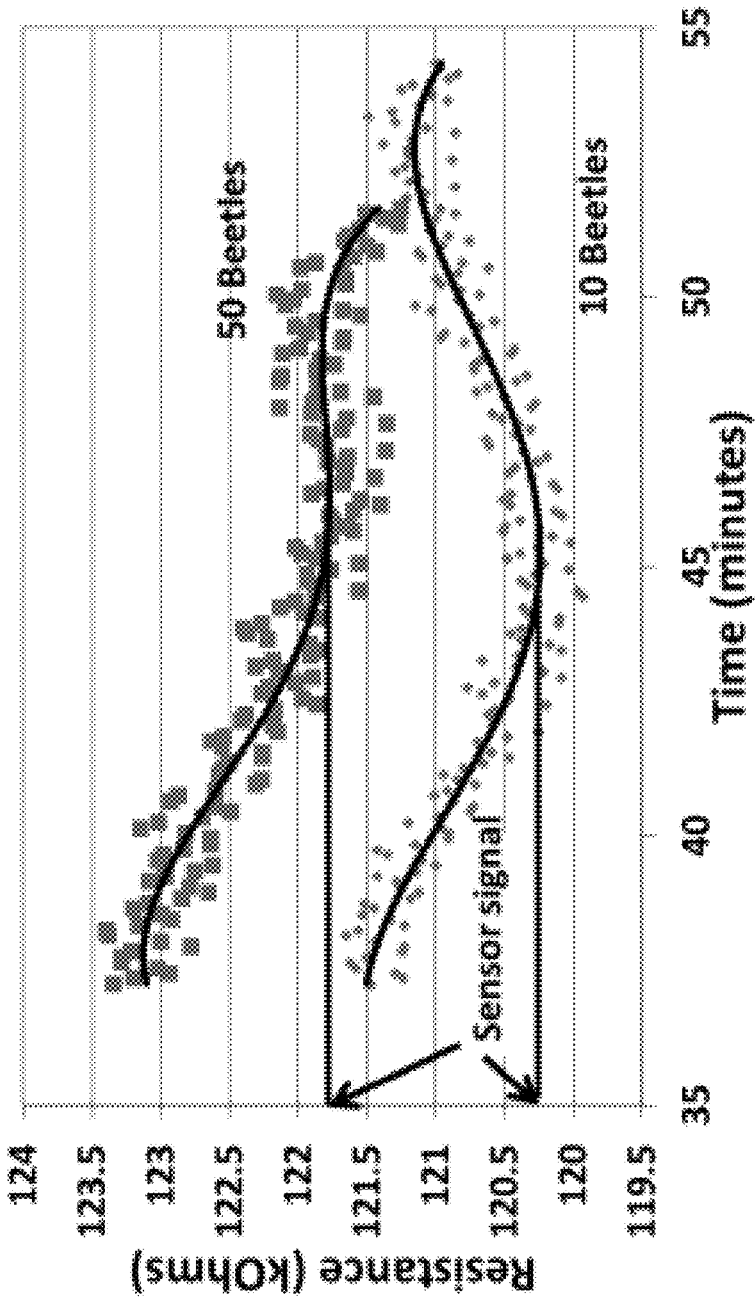
FIGS. 11A-11C are graphs illustrating the response of a third VOC sensor to the presence of three target stored product insects ("SPIs") in accordance with one embodiment of the subject application.
Figure 11B:
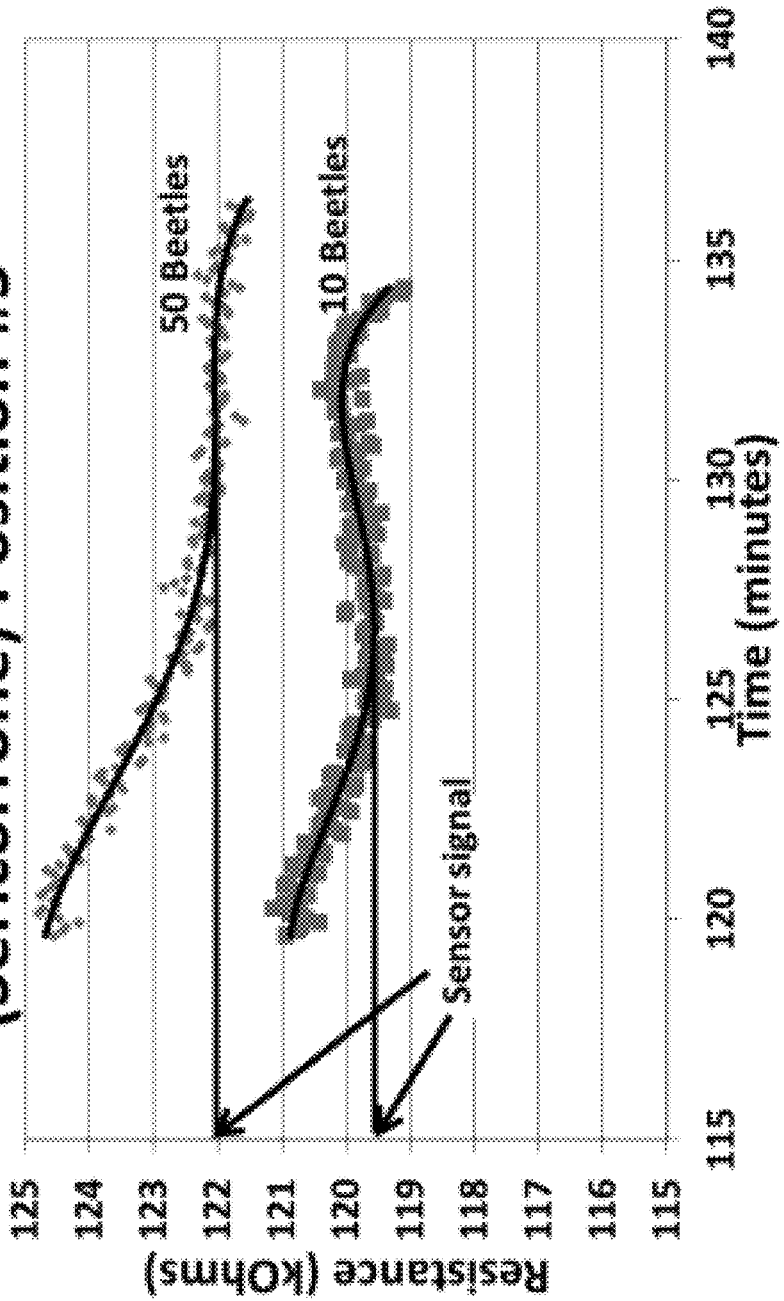
Figure 11C:
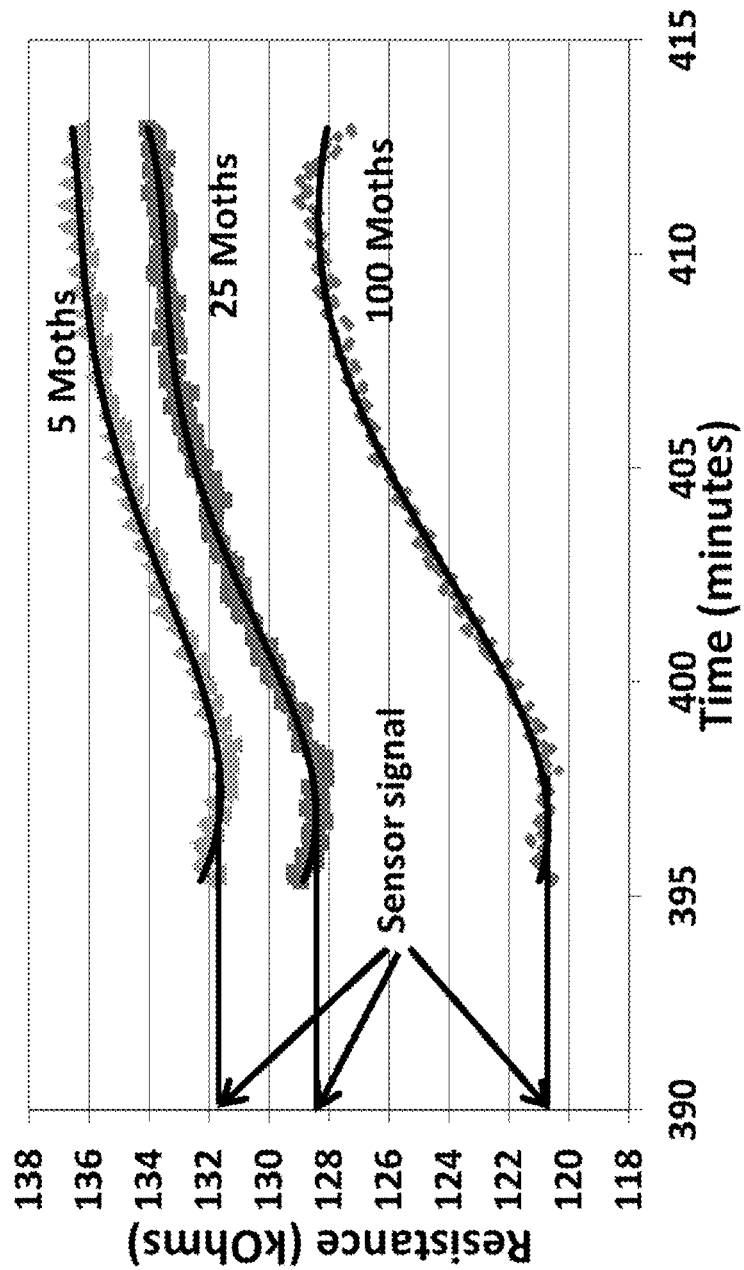

With reference to FIGS. 8A-8D, provided are graphs of laboratory bench tests of various embodiments of VOC sensor chips and their sensitivity to pheromones. Adult insect pheromones were made into test gases at a concentration of 2 ppm in dry nitrogen in an A31 compressed gas cylinder. This test gas was diluted with additional dry nitrogen to achieve a gas stream with pheromone concentrations between 100 ppb and 300 ppb. This gas stream was injected into the pre-prototype device and the net conductance was determined. The following charts show the response of five different sensors, one with no catalyst added, four with the catalysts Pd, Pt, Os and W added. The W catalyst provides excellent sensitivity for the IMM pheromone (FIG. 8A), for the cigarette beetle pheromone (FIG. 8C), and for the warehouse beetle pheromone (FIG. 8D). The Pd catalyst shows excellent sensitivity for the red flour beetle pheromone (FIG. 8B). The other catalysts are less effective in sensitive response to the pheromones.

Figure 12A:
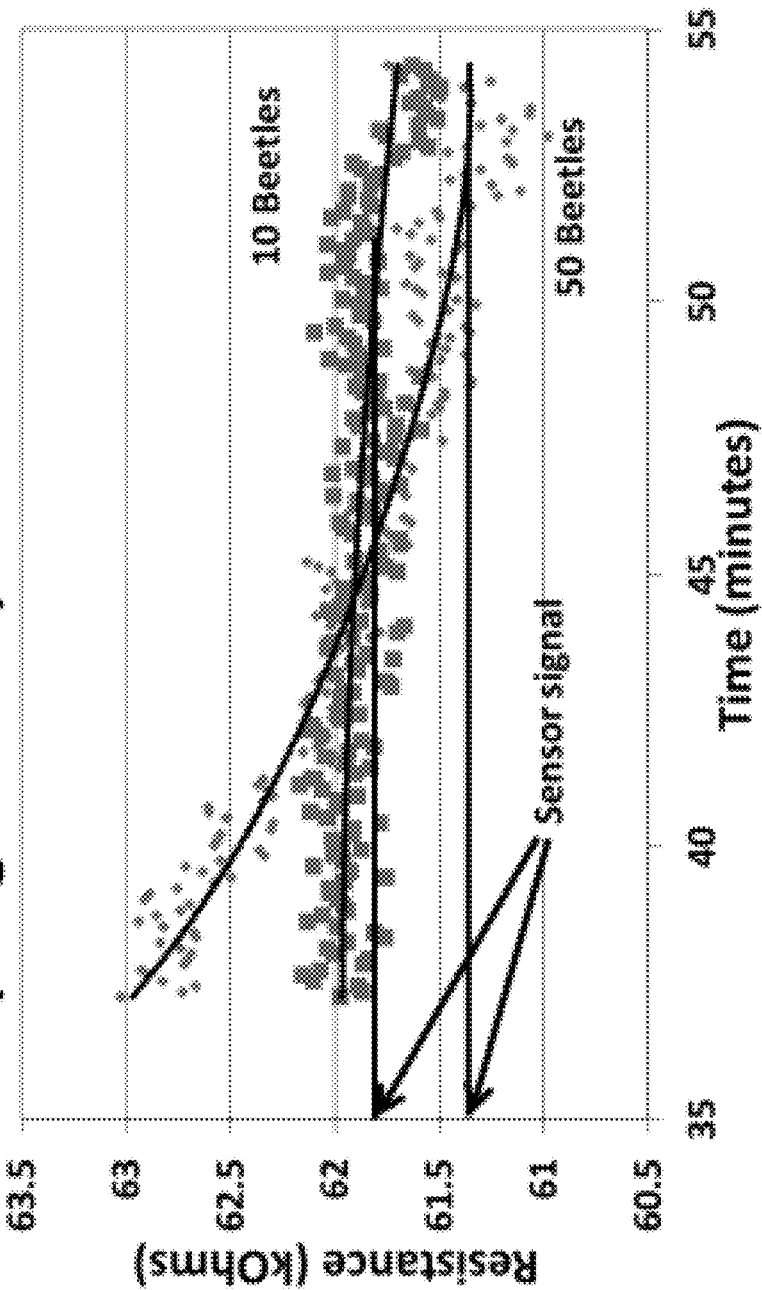
FIGS. 12A-12C are graphs illustrating the response of a fourth VOC sensor to the presence of three target stored product insects ("SPIs") in accordance with one embodiment of the subject application.
Figure 12B:
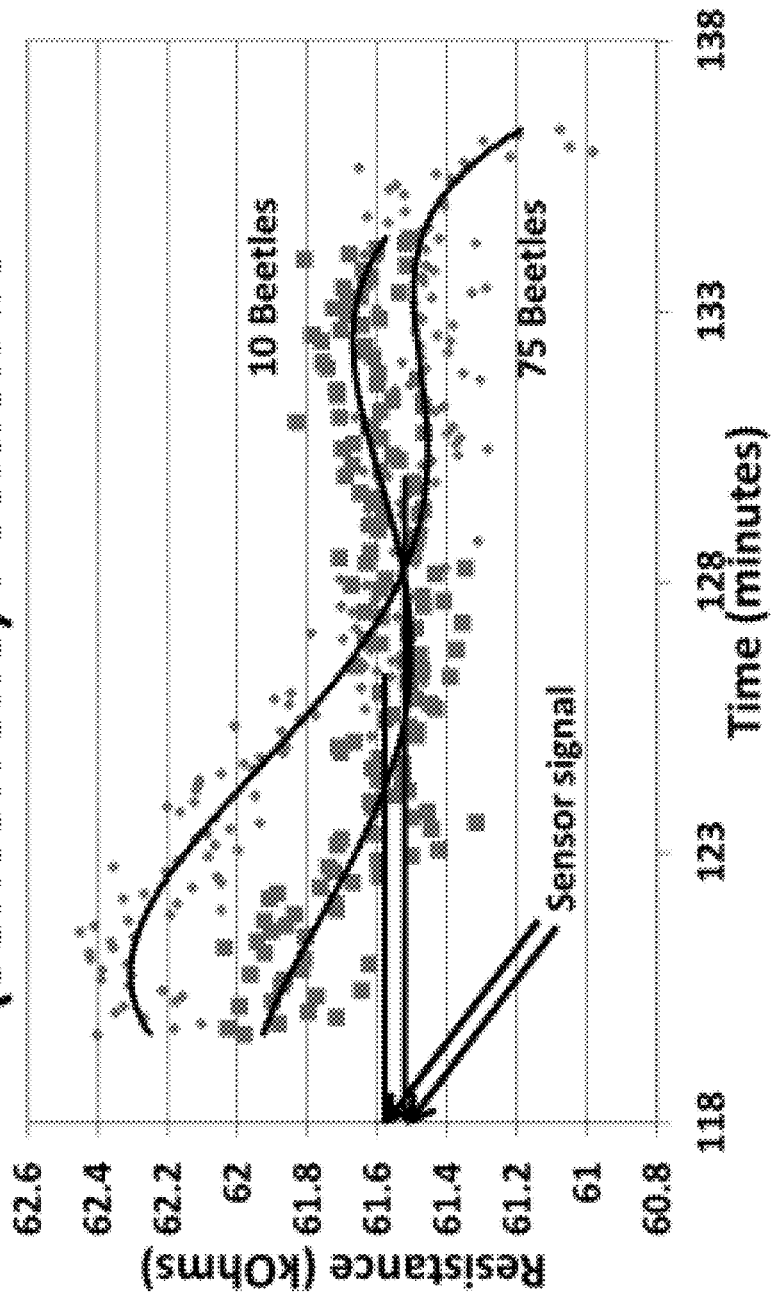
Figure 12C:
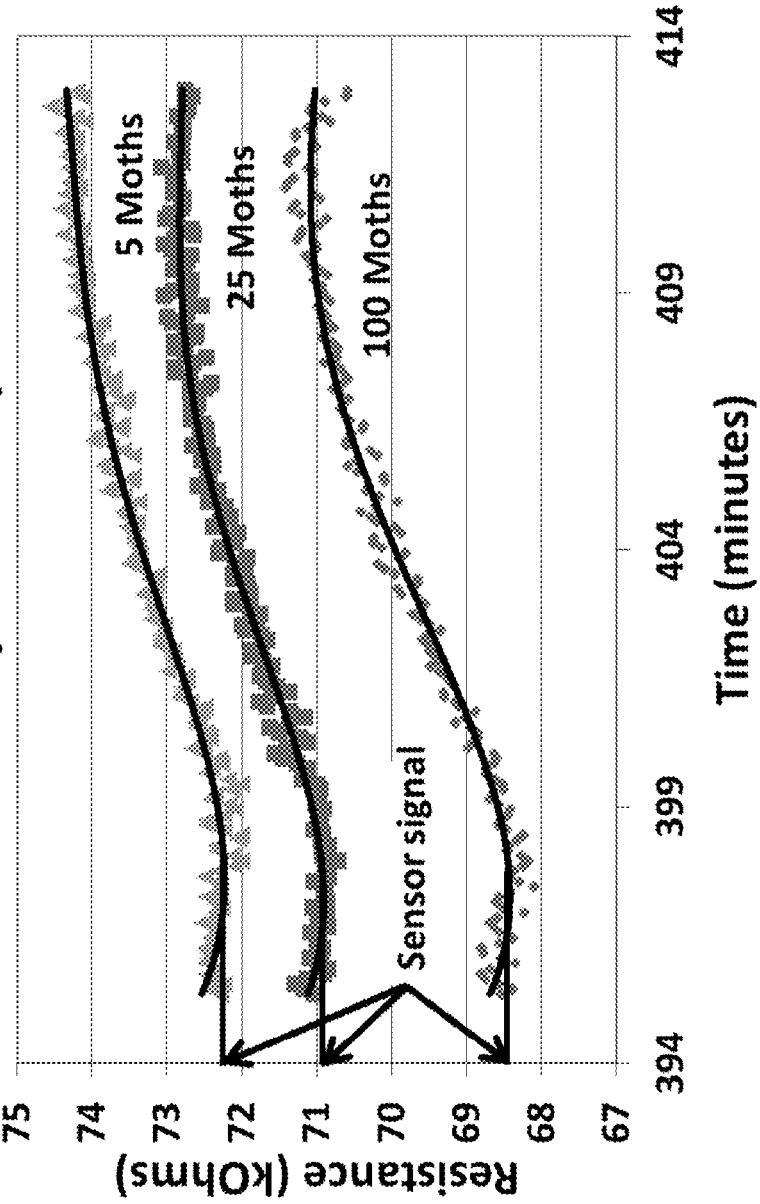
Figure 13A:
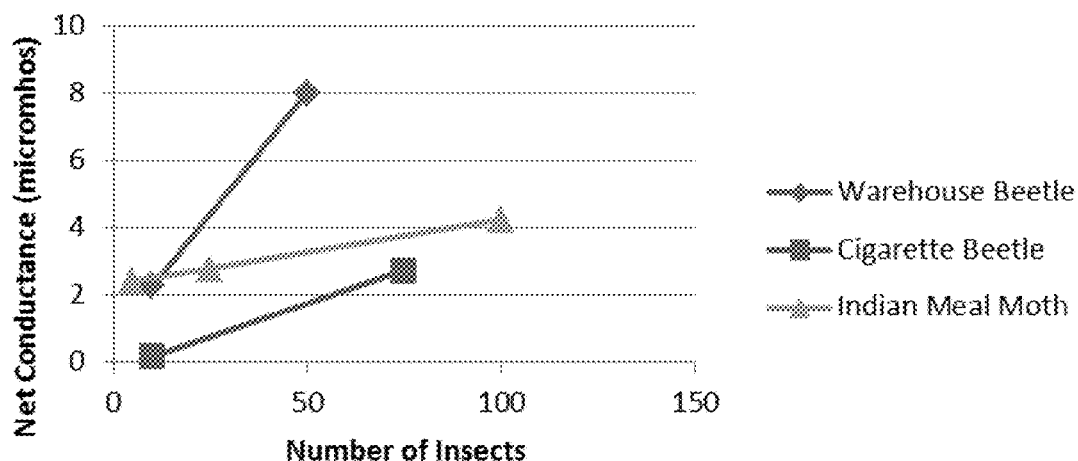
FIGS. 13A-13D are graphs illustrating the response of four VOC sensors to the presence varying quantities of three target stored product insects ("SPIs") in accordance with one embodiment of the subject application.
Figure 13B:
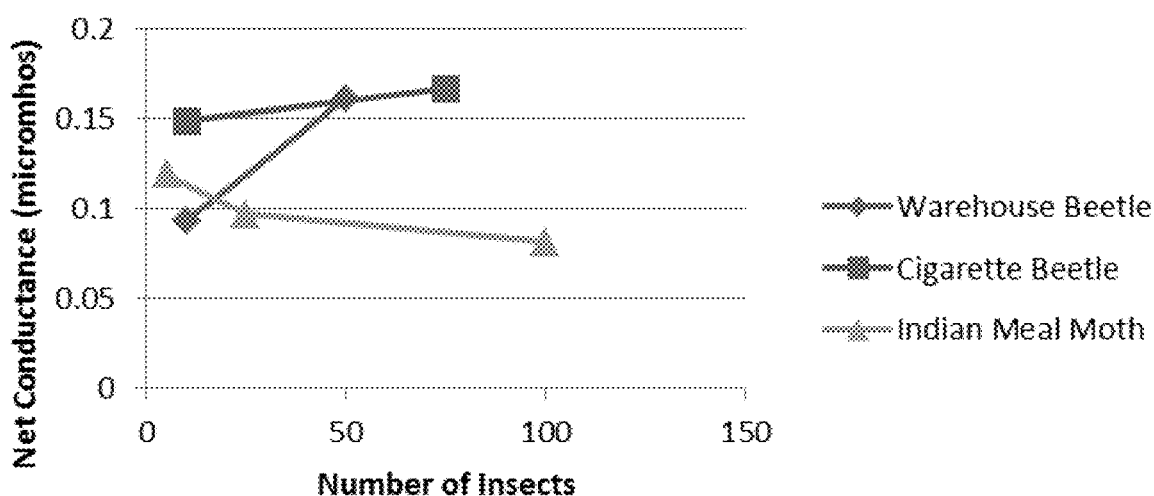
Figure 13C:
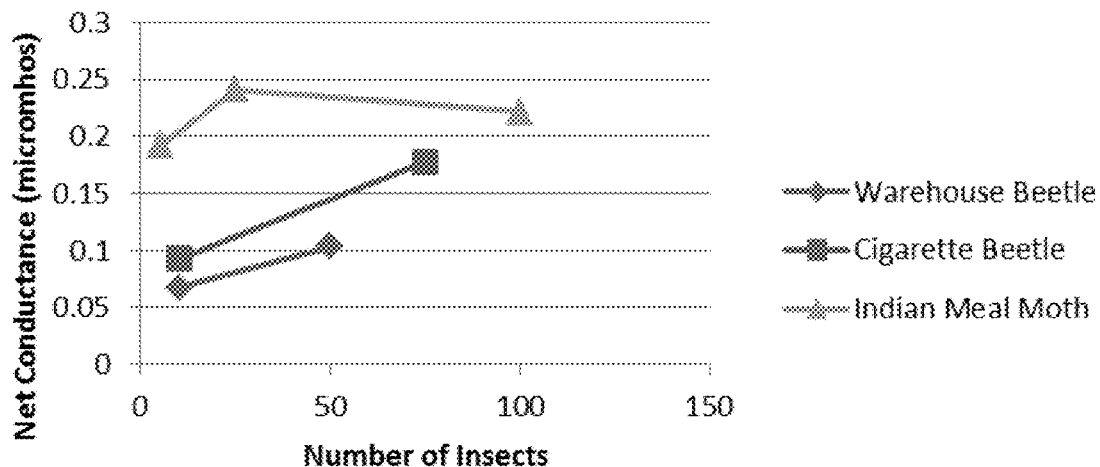
Figure 13D:
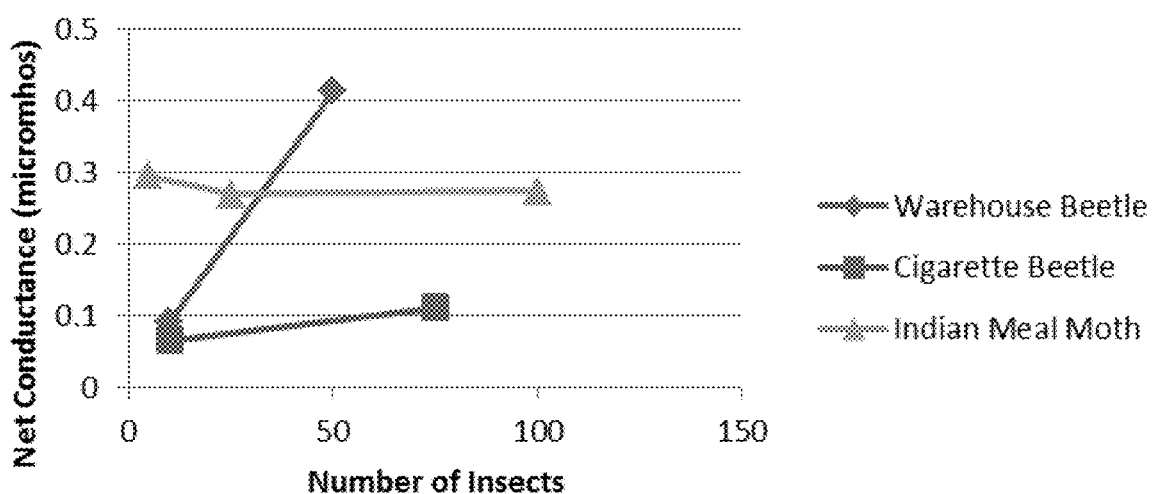

With reference to FIGS. 9A-9C, FIGS. 10A-10C, and FIGS. 11A-11C, provided are experimental results of field testing of sensor chip response to headspace over products with insects. In a field trial, the headspace gas over a 10 lb sample of clean white wheat flour was injected into the pre-prototype device to establish a baseline resistance value. Once the baseline resistance value was established, the headspace gas over a companion 10 lb sample of clean white wheat flour into which vials containing different numbers of the four live insects, IMM, red flour beetle, warehouse beetle and cigarette beetle were injected. The resistance data for the headspace gas over product with live insects embedded is shown for an uncatalyzed chip (FIGS. 9A-9B), a Pt-catalyzed chip (FIGS. 10A-10C), an Os-catalyzed chip (FIGS. 11A-11C), and a W-catalyzed chip (FIGS. 12A-12C).

As seen in each case, a decrease in resistance is clear with an increase in insect population. Additional insects produce additional pheromone in the headspace. A higher pheromone concentration causes a reduction in sensor chip resistance. Thus, the sensor chips are able to produce a signal dependent on the insect population. This signal can be analyzed and a correlation between insect population and signal can be established.

With respect to FIGS. 13A-13D, graphs are provided showing the analytical results of the data discussed above. The raw data was analyzed by converting the chip resistance values, R, into chip conductance values, mathematically represented as K. The net conductance was determined by subtracting the chip conductance when no insects are present, $K_b$, from the chip conductance when insects are present, $K_g$. The net conductance is represented as $\Delta K$ mathematically. Plots of $\Delta K$ vs insect number are shown in FIGS. 13A-13D. As a result, these plots allow for selection of the best catalyst for each pheromone: an uncatalyzed chip for IMM; an Os catalyzed chip for warehouse beetle; and an uncatalyzed chip for cigarette beetle, for example.

The present specification has been set forth with reference to preferred embodiments. Obviously, modifications and alterations will occur to others upon reading and understanding the present specification. It is intended that the invention be construed as including all such modifications and alterations insofar as they come within the scope of the appended claims or the equivalents thereof. That is to say, it will be appreciated that various of the above-disclosed and other features and functions, or alternatives thereof, may be desirably combined into many other different systems or applications, and also that various presently unforeseen or unanticipated alternatives, modifications, variations or improvements therein may be subsequently made by those skilled in the art which are similarly intended to be encompassed by the following claims.

What is claimed is:

1. A method of identifying an insect infestation of a stored product by detecting one or more target volatile organic compounds (VOCs) within a target fluid flow, the method comprising:
    providing a device that comprises:
        a sensor array including a plurality of VOC sensors, wherein each VOC sensor comprises:
            a substrate having a first and second side;
            a resistive heater circuit formed on the first side of the substrate;
            a sensing circuit formed on the second side of the substrate; and
            a chemically sensitive film formed over the sensing circuit on the second side of the substrate;
    heating one or more of the plurality of VOC sensors to at least a first operating temperature, wherein at least a first VOC sensor is heated to the first operating temperature and at least a second VOC sensor is heated to a second operating temperature, the second operating temperature being different from the first operating temperature;
    contacting the one or more VOC sensors with the target fluid flow;
    determining a set of conductance change values ($\Delta K_i$) corresponding to each of the one or more VOC sensors contacted with the target fluid flow;
    determining a gas component concentration ($[X]_n$) for one or more of the target VOCs within the target fluid flow based on the set of conductance change values;
    determining one or more specific net conductance values for one or more of the VOC sensors, wherein each specific net conductance value corresponds to one of the target VOCs;
    wherein the gas component concentration ($[X]_n$) for the one or more target VOCs within the target fluid flow is determined based on the set of conductance change values ($\Delta K_i$) and the one or more specific net conductance values for each of the one or more of VOC sensors;
    wherein each specific net conductance value corresponding to a single target VOC is determined by:
        contacting the one or more VOC sensors with a control fluid flow having a known concentration of the single target VOC;
        measuring a test conductance for each of the one or more VOC sensors; and
        for each of the one or more VOC sensors, calculating a specific net conductance value based on the measured test conductance of the VOC sensor and the known concentration of the single target VOC within the control fluid flow; and
    determining a plurality of specific net conductance values for one or more of the VOC sensors, wherein each of the specific net conductance values for each of the VOC sensors corresponds to a different single target VOC.

2. The method of claim 1, wherein the method further comprises:
    measuring a signal conductance for the one or more VOC sensors after contacting the one or more VOC sensors with a multi-component target fluid flow;
    wherein the set of conductance change values ($\Delta K_i$) is determined based on the difference between the signal conductance for each of the one or more VOC sensors contacted with the multi-component target fluid flow and a baseline conductance of each of the corresponding VOC sensors.

3. The method of claim 2, wherein the baseline conductance for the one or more VOC sensors is measured while the one or more VOC sensors are in an atmosphere absent of any target VOCs.

4. The method of claim 3, wherein the method further comprises:
    adjusting the baseline conductance of one or more of the VOC sensors after being contacted with at least one target VOC to match the baseline conductance of the corresponding VOC sensor prior to contact with the at least one target VOC, wherein the baseline conductance is adjusted by heating one or more of the VOC sensors to at least a second operating temperature.

5. The method of claim 2, wherein the method further comprises:
    contacting one or more of the plurality of VOC sensors with a sample fluid flow, the sample fluid flow being absent of any target VOCs; and
    measuring the baseline conductance for the one or more VOC sensors.

6. The method of claim 1, wherein the first operating temperature is between about 180° C. and about 400° C.

7. The method of claim 1, wherein the target fluid flow is an air sample taken from within a proximity to the stored product being evaluated.

8. A device for detecting one or more target volatile organic compounds (VOCs) within a target fluid flow, the device comprising:
    a sensor array having a plurality of VOC sensors, wherein each VOC sensor includes:
        a substrate;
        a resistive heater circuit formed on a first side of the substrate;
        a sensing circuit formed on a second side of the substrate; and
        a chemically-sensitive film formed over the sensing circuit on the second side of the substrate;
    wherein the resistive heater circuit of a first VOC sensor of the sensor array is configured to heat the first VOC sensor to a first operating temperature, and the resistive heater circuit of a second VOC sensor of the sensor array is configured to heat the second VOC sensor to a second operating temperature, the second operating temperature being different from the first operating temperature;
    wherein the sensor array is operatively connected to a controller, the controller being configured to:
        measure a conductance for one or more of the plurality of VOC sensors; and determine a set of conductance change values corresponding to each of the one or more VOC sensors contacted with the target fluid flow; and determine a gas component concentration for one or more of the target VOCs within the target fluid flow based on the set of conductance change values;

determine one or more specific net conductance values for one or more of the VOC sensors, wherein each specific net conductance value corresponds to one of the target VOCs;

wherein the gas component concentration ($[X]_n$) for the one or more target VOCs within the target fluid flow is determined based on the set of conductance change values ($\Delta K_i$) and the one or more specific net conductance values for each of the one or more of VOC sensors;

wherein each specific net conductance value corresponding to a target VOC is determined by:
  contacting the one or more VOC sensors with a control fluid flow having a known concentration of the target VOC;
  measuring a test conductance for each of the one or more VOC sensors; and
  for each of the one or more VOC sensors, calculating a specific net conductance value based on the measured test conductance of the VOC sensor and the known concentration of the target VOC within the control fluid flow; and determine a plurality of specific net conductance values for one or more of the VOC sensors, wherein each of the specific net conductance values for each of the VOC sensors corresponds to a different target VOC.

9. The device of claim 8, wherein the sensor array comprises from about two to about ten VOC sensors.

10. The device of claim 8, wherein the resistive heater circuit of at least one of the plurality of VOC sensors is a serpentine pattern having a longitudinal trace width from about 0.288 mm to about 0.352 mm and a longitudinal trace spacing width from about 0.333 mm to about 0.407 mm.

11. The device of claim 8, wherein the sensing circuit of at least one of the plurality of VOC sensors includes a first sensing element and a second sensing element forming a pair of extended inter-digitated contacts;
  wherein the first sensing element comprises a plurality of extended contacts, each contact having a latitudinal trace width of from about 0.162 mm to about 0.198 mm and a latitudinal trace spacing of from about 0.738 mm to about 0.902 mm; and
  wherein the second sensing element comprising a plurality of extended contacts, each contact having a latitudinal trace width of from about 0.162 mm to about 0.198 mm and a latitudinal trace spacing of from about 0.738 mm to about 0.902 mm.

12. The device of claim 11, wherein each of the first and second sensing elements comprise at least three extended contacts, and wherein the sensing circuit has a latitudinal trace spacing between each extended contact of the first and second sensing elements of from about 0.288 mm to about 0.352 mm.

13. The device of claim 8, wherein at least one of the resistive heater circuit and the sensing circuit is formed from a composition comprising platinum, and the chemically sensitive film is a nano-crystalline tin oxide film formed from an aqueous tin oxide gel.

14. The device of claim 8, wherein the chemically sensitive film comprises a doping agent selected from a group consisting of: platinum; palladium; molybdenum; tungsten; nickel; ruthenium; and osmium.

* * * * *